(12) United States Patent
Kurt-Elli

(10) Patent No.: US 7,428,475 B2
(45) Date of Patent: Sep. 23, 2008

(54) METHOD OF PROCESSING OSCILLATORY DATA

(75) Inventor: Hilmi Kurt-Elli, Derby (GB)

(73) Assignee: Rolls-Royce PLC, London (GB)

( * ) Notice: Subject to any disclaimer, the term of this patent is extended or adjusted under 35 U.S.C. 154(b) by 176 days.

(21) Appl. No.: 10/584,938

(22) PCT Filed: Dec. 2, 2004

(86) PCT No.: PCT/GB2004/005055

§ 371 (c)(1),
(2), (4) Date: Aug. 7, 2006

(87) PCT Pub. No.: WO2005/068949

PCT Pub. Date: Jul. 28, 2005

(65) Prior Publication Data

US 2008/0034870 A1 Feb. 14, 2008

(30) Foreign Application Priority Data

Jan. 15, 2004 (GB) ................................. 0400840.5

(51) Int. Cl.
*G06F 15/00* (2006.01)
*G01R 23/00* (2006.01)
*G01H 1/00* (2006.01)

(52) U.S. Cl. ............................ 702/191; 702/77; 73/579; 73/660

(58) Field of Classification Search .................. 702/56, 702/76, 77, 79, 189, 190; 73/657, 660, 579; 331/65

See application file for complete search history.

(56) References Cited

U.S. PATENT DOCUMENTS 4,123,940 A * 11/1978 Herzl et al. .............. 73/861.24
4,290,145 A 9/1981 Saba et al.
5,068,800 A 11/1991 Brook et al.
5,450,760 A * 9/1995 Lew et al. ................. 73/861.77
6,474,166 B1 11/2002 Osawa et al.
2002/0040278 A1 4/2002 Anuzis et al.

OTHER PUBLICATIONS

S. P King et al.; "The use of Novelty Detection Techniques for monitoring High-Integrity Plant;" Proceedings of the IEEE International Conference on Control Applications; Sep. 18-20, 2002; pp. 221-226.
R. J. Allwood et al.; "The automatic interpretation of vibration data from gas turbines;" *The Aeronautical Journal*; vol. 100, No. 993; Mar. 1996; pp. 99-107.
Bendat et al., "Random Data: Analysis and Measurement Procedures," Wiley-Interscience, a division fo John Wiley & Sons, Inc., pp. 82-85 and 360-364, 1971.

* cited by examiner

*Primary Examiner*—Bryan Bui
(74) *Attorney, Agent, or Firm*—Oliff & Berridge, PLC

(57) ABSTRACT

A method which permits the transformation of non-stationary response measurements into stationary data for analysis is provided. Many standard analysis techniques, particularly for oscillatory responses, are based on stationary data, and the method allows these techniques to be performed on originally non-stationary data. The method may be a method of processing oscillatory response data from a resonant system including: obtaining data measuring an oscillatory response of the system; estimating the variation in natural frequency of a mode of said response; filtering the data around a selected frequency to obtain a filtered response; determining a carrier signal whose frequency variation with respect to time is equal in magnitude to said estimated variation in natural frequency; and modulating the amplitude of said carrier signal using said filtered response to obtain a modulated carrier signal. A corresponding system for processing oscillatory response data is also provided.

18 Claims, 19 Drawing Sheets

Bandpass Filtered
Response

50            Time            50.3s

Carrier Signal

50            Time            50.3

Modulated signal

50 — Time — 50.3s

ZMOD or Waterfall of Transformed Data $\left(\dfrac{f}{\Delta f}\right)$

Time ⟶

Schematic of ZMOD for Data
Prior to Transformation

Schematic of ZMOD for Data
After Transformation

METHOD OF PROCESSING OSCILLATORY DATA

SUMMARY

The present invention relates to a method of processing oscillatory data. It is particularly, but not exclusively, concerned with a method of processing oscillatory response data, and in particular non-stationary responses caused for example by a characteristic frequency of a system changing with time.

There are many situations where the response of a system, such as a gas turbine engine or a component thereof, which is subjected to random or engine order (EO) excitations, displays non-stationary characteristics. These may occur even where the excitation itself is reasonably stationary.

For EO excitation, engine speed changes will cause a varying response level as the EO frequency approaches or moves away from a modal frequency. Thus the response of the system will be transient in nature and non-stationary in that sense. If, in addition, the modal frequency in question is itself changing with time or engine speed, then the transient response will be further affected, resulting in a complex speed, or time, response profile.

Random excitation data is normally considered stationary if statistical properties such as long time averaged root-mean-square level in a frequency band are constant with time. The non-stationary case can arise if the modal frequencies are changing with time.

Changes in modal frequency can occur for a variety of reasons. For example, in a gas turbine engine, these variations can be due to thermal and/or centripetal force stiffening. Within missile systems these variations may also be due to mass loss effects.

In mechanical systems, damping provides a measure of the energy dissipation capacity of a structure or system. The measurement of damping can be useful because it aids the understanding of the behaviour of a structure, and knowledge about the level of damping can be valuable in troubleshooting and assessment of potential and actual problem fixes. Damping can also be used to provide parameter values for and validation of models.

Changes in damping over time may be useful to indicate the "health" of a system, and can also be used to provide an indication of potential instability of a system such as "flutter".

It is difficult to determine the characteristics of a mode exhibiting such non-stationary behaviour, arising due to modal frequencies changing with time. For example it is difficult to determine the modal bandwidth or damping associated with the mode.

This is because conventional analysis methods and systems do not adequately handle non-stationary data such as that discussed above, and therefore it is difficult to obtain accurate measurements of any of the above characteristics in systems displaying non-stationary characteristics.

In practice the most common approach used for dealing with non-stationary random excitation data at the moment is the segmented approach outlined in *Random Data: Analysis and Measurement Process* by J. S. Bendat and A. G. Piersol; Wiley Interscience, 1971. We are not aware of any conventional approach which deals with EO data and compensates for changes in the non-stationary mode characteristic data.

The segmented approach splits the oscillatory response data into segments, each of which are considered to be stationary and therefore processed as such in the normal manner. The above reference describes why results from this approach should be treated with caution and may only be useful in a qualitative sense.

Specifically, a problem arises with the short time interval bias error arising from changes in the characteristics which occur within the period of an individual segment, e.g. if the modal frequency changes significantly relative to the modal bandwidth within a segment. In order to suppress the time interval bias error, a short averaging time (subrecord length) T is required, but to obtain the desired spectral decomposition, a narrow resolution bandwidth $B_e$ is required. The result is a relatively small $B_e.T$ product and hence a large random error.

However, in many cases the requirement for adequate frequency resolution will mean that segment durations are long, with significant modal frequency changes relative to the modal bandwidth and therefore a serious bias occurs in the bandwidth or damping estimates.

Therefore the segmented approach is in principle problematic and in some situations may not even allow qualitative results to be obtained.

The present invention seeks to address some or all of the problems associated with the segmented approach. An aspect of the present invention also seeks to provide a methodology for handling EO data.

In general terms, the present invention provides a method which permits the transformation of non-stationary response measurements into stationary data for analysis.

The present invention relates to oscillatory systems in general, but will be described and illustrated for oscillatory data which specifically describes vibration phenomena. Alternative applications of the invention, for example in electrical networks in which it is desired to determine the bandwidth when the characteristic frequency of the circuit is changing with time, are equally possible.

A first aspect of the present invention provides a method of processing oscillatory response data from a resonant system comprising:

obtaining data measuring an oscillatory response of the system;

estimating the variation in natural frequency of a mode of said response;

filtering the data around a selected frequency to obtain a filtered response;

determining a carrier signal whose frequency variation with respect to time is equal in magnitude to said estimated variation in natural frequency; and modulating the amplitude of said carrier signal using said filtered response to obtain a modulated carrier signal.

The selected frequency around which the data is filtered may be the natural frequency of a mode of the response (and preferably the mode which is the subject of the estimating step) or the frequency of an engine order. In frequency terms, the filtering may be static (e.g. centred on a fixed frequency) or dynamic (e.g. centred on a varying frequency).

The frequency variation of the carrier signal may be equal to the estimated variation in natural frequency or may be the negative of the estimated variation.

Preferably the frequency of the carrier signal is greater than the difference between the highest and lowest values of the natural frequency of said mode over the period of interest. This may allow the data from two sidebands formed in said modulated carrier signal to be analysed separately with no overlap between them.

Transforming the typically non-stationary oscillation data according to the method of the present aspect may make it effectively stationary, and thus in a more useful form for further analysis.

The step of estimating the change in natural frequency may include obtaining multiple Fourier transforms of the measured data, for example as described in "The automatic interpretation of vibration data from gas turbines", Allwood, King & Pitts, *The Aeronautical Journal of the Royal Aeronautical Society*, March 1996.

Alternatively to the methods described in this reference, the same zmod (waterfall or Campbell diagram) data containing the multiple Fourier transform data may be analysed to determine likely natural frequency values via a standard modal curve fitting approach and/or by manually cursoring likely estimates prior to conducting a least squares type fit to the data to determine a smooth time frequency profile.

Alternatively, for example where the mode is remote from others and the response may be bandpass filtered around the mode, the step of estimating the change in natural frequency may include calculating a running average of the instantaneous frequency of the response.

Furthermore, model data or a combination of model data with experimental data may be used in the step of estimating the change in natural frequency.

The step of estimating the variation in the natural frequency of the mode of the response may also include further steps which fine-tune the estimation. For example, an optimisation approach may be used to alter the natural frequency variation, under predetermined constraints, in order to minimise the modal bandwidth associated with the transformed data and mode of interest. The constraints may impose limits on the smoothness associated with the functional form of the natural frequency estimate versus time. For example, changes which are considered not to be smooth enough, or which are considered to be too quick might be rejected as unrealistic.

When the data being processed comes from engines or, in particular, gas turbines, in many cases it will have arisen from conducting engine speed-up or slow-down tests in which the engine speed changes over a given time interval. Under these conditions it is common for the natural frequency variation with time to be approximated by a quadratic equation because of the long time constant associated with the thermal or centrifugal-force-stiffening effects causing the natural frequency changes. Higher degree polynomial approximations or other functional forms or numerically described profiles could also be used. Numerically described profiles could, for example, be obtained by tracking the peak on a running spectrum.

An advantage of the method of processing of this aspect is that modes which are close in frequency terms to the mode being identified are effectively "smeared" in frequency by the time averaging process if their natural frequency time profile differs from that of the mode being identified. This increases the likelihood of the mode of interest being identified, and allows better estimation of modal bandwidths from a single mode estimation methodology.

Another aspect of the present invention provides a method of analysing a resonant system, including the steps of: processing according to the above aspect; and analysing the modulated carrier signal to determine one or more characteristics of the system.

As a result of the transformation of the response data, standard analysis techniques may be used on the modulated carrier signal to determine features of interest such as bandwidth and damping, and when the data being analysed is effectively stationary, the analysis may be done with high frequency resolution and long averaging times, without bias errors resulting from natural frequency changes.

For example, the step of analysing may include determining a power spectral density (PSD) function of the modulated carrier signal.

Alternatively, if the input, which is driving the system, is known, a frequency response function computation may be conducted. Again due to the processing of the data, standard random data analysis techniques may be used.

A further advantage of the methods of the present invention is that bias (or other systematic) errors in the natural frequency estimation may be tolerated since the modal bandwidth is unaffected by the transformation and bias errors in the natural frequency simply affect the apparent frequency of a mode which has been made stationary.

For EO excitation a further advantage of the methods of the present invention is that it enables a modal curve fitting approach to be used on the transformed data, even if the EO does not fully traverse the mode; i.e. the skirts or only part of the resonance curve profile may be analysed to determine damping, even when the engine speed falls short of causing the relevant EO frequency to equal and exceed the modal frequency.

The methods of the previous aspects may conveniently be implemented in software, for execution on any appropriate digital computer. The software may also embody preferred or optional features of the methods of the previous aspects. The methods may be performed on-line, or off-line on stored measurement data.

Thus further aspects of the invention respectively provide a computer system operatively configured to implement any of the methods of the previous aspects of the invention; computer programming product or products (such as ROM, RAM, floppy discs, hard drives, optical compact discs, magnetic tapes, and other computer-readable media) carrying computer code for implementing any of the methods of the previous aspects of the invention; and a computer program per se for implementing any of the methods of the previous aspects of the invention.

Further aspects of the present invention also provide apparatuses for carrying out the methods of the above aspects.

In particular, these aspects provide an apparatus for processing oscillatory response data from a resonant system, the apparatus including:

a sensor for measuring an oscillatory response of the system; and a processor which is adapted to:

receive measurement data from the sensor;

estimate from the data the variation in natural frequency of a mode of said response;

filter the data around a selected frequency to obtain a filtered response;

determine a carrier signal whose frequency variation with respect to time is equal in magnitude to said estimated change in natural frequency; and modulate the amplitude of said carrier signal using said filtered data.

In an apparatus for analysing the resonant system, the processor may be further adapted to analyse the modulated carrier signal to determine one or more characteristics of the system.

The processor may be implemented in dedicated hardware, or it may be a suitably programmed computer.

Preferred or optional features of the methods of the previous aspects may be embodied in corresponding preferred or optional features of the apparatus of this aspect.

The system of any of the above aspects may be a model system. Alternatively the system may be a mechanical system, such as a gas turbine engine or a component thereof. Alternatively the system may be an electrical network.

BRIEF DESCRIPTION OF THE DRAWINGS

An embodiment of the present invention will now be described in relation to the accompanying drawings, in which.

DETAILED DESCRIPTION

General Theory

Figure 1:
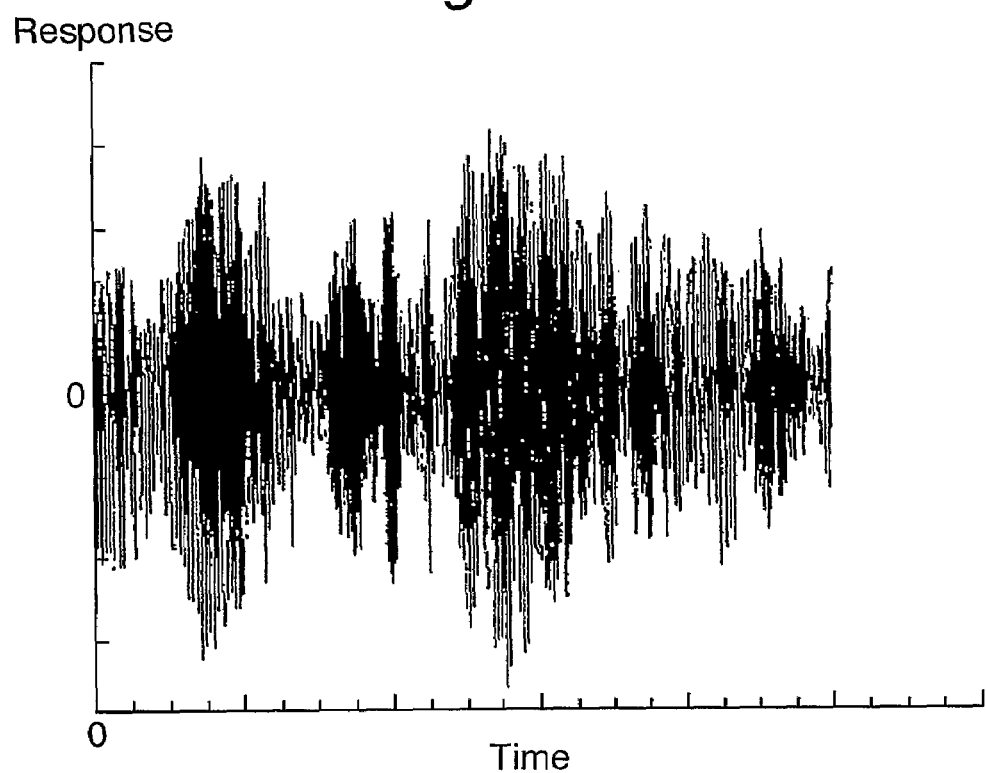
FIG. 1 shows an oscillatory response of a model system.

A general theory of embodiments of the present invention is set out below.

For this purpose, the systems to which the embodiments of the invention are applied are considered to have an input x(t) and an output y(t), both of which are functions of time t. The output may represent a measured or predicted response.

A mode of interest of the system has an angular modal frequency, the natural frequency, which also changes with time. An approximate description of its angular frequency profile $\omega_n(t)$ is obtained, for example by processing y(t) by zmod plotting, bandpass filtering, zero crossing analysis, etc., and/or making use of model data.

It is desired to transform y(t) to compensate for the non-stationary behaviour associated with the frequency changes of the mode. The invention accomplishes this by amplitude modulating y(t) with a carrier signal whose frequency also changes, in a synchronous manner with the mode frequency. Although the term carrier signal is used in this specification, the signal formed is quite different from normal carrier signals, formed for example in communications technology, in that it varies with the natural frequency.

Thus a varying carrier angular frequency is created:

$$\omega_c(t) = \omega_s - [\omega_n(t) - \omega_n(t^*)] \qquad \text{Equation (1)}$$

where: $\omega_n(t^*)$ is the value at some arbitrarily chosen instant (e.g. $t^* = 0$ or when the response peaks), and $\omega_s$ is a constant shift frequency that places signal components associated with the mode of interest of the transformed signal into another part of the spectrum. $\omega_s$ is chosen so as to be sufficiently large to ensure that the lower and upper sideband components of the modulated response (see below) are adequately separated in frequency.

Note that since $\omega_s$ and $\omega_n(t^*)$ are both constants, they could in fact be incorporated into a single constant term ($\omega_{constant}$); e.g. the carrier frequency then becomes $\omega_c(t) = \omega_{constant} - \omega_n(t)$. In some applications it may be more convenient to think in terms of the form expressed in equation (1) although both are equally valid.

Similarly, the carrier frequency for the lower sideband formulation (described below) could equally be defined as $\omega_c(t) = \omega_{constant} + \omega_n(t)$.

The phase $\theta_c(t)$ of the carrier signal is obtained by integrating $\omega_c(t)$. The phase at $t = 0$ may be arbitrarily set (e.g. to zero). The integration may be done by a variety of well known techniques, such as the first order Taylor approximation for a discrete process:

$$\theta_c(t) \approx \theta_c(t - dt) + \{dt \cdot \omega_c(t - dt)\}$$

where dt is the time interval of integration.

The carrier signal then becomes:

$$s_c(t) = \sin\{\theta_c(t)\}$$

although of course a cosine function could also have been chosen since the initial phase is arbitrary—the requirement being simply that the rate of change of the phase $\theta_c(t)$ equals the carrier frequency $\omega_c(t)$ as defined above.

A modulated or transformed signal $y_m(t)$ is then obtained by multiplying the signal $y(t)$ by $s_c(t)$:

$$y_m(t) = s_c(t).y(t).$$

This results in a time dependent transformation of frequencies in a continuous manner, enabling further analysis using standard stationary data analysis techniques to yield bandwidth and damping information. The mode of interest now appears to be stationary with an angular frequency equal to $[\omega_s+\omega_n(t^*)]$ when looking at the upper sideband data of the modulated signal.

The basic modulation effect and the "upper" and "lower" sideband" terminology can be appreciated by considering the simple case where $s_c(t)=\sin(\theta)$ and $y(t)=\cos(\phi)$, in which case $y_m(t)=s_c(t).y(t)=\frac{1}{2}.[\sin(\theta-\phi)+\sin(\theta+\phi)]$. $(\theta-\phi)$ is referred to as the lower sideband component and $(\theta+\phi)$ is referred to as the upper sideband component of the modulated signal. The upper sideband component has an angular frequency which is the time rate of change of $(\theta+\phi)$, which in turn is equal to the time rate of change of each of $\theta$ and $\phi$ separately—i.e. the sum of the instantaneous frequencies associated with the carrier and original response signals.

Thus, for the case where the signal $y(t)$ has a time varying frequency component of $\{\omega_n(t)+\Delta\}$ where $\Delta$ is constant, then (from equation 1) and the above it can be seen that this component is transformed to an upper sideband frequency of:

$$\{\omega_n(t)+\Delta\}+\{\omega_s-[\omega_n(t)-\omega_n(t^*)]\}=\{\omega_s+\omega_n(t^*)+\Delta\},$$ which is a constant, as it has no time varying components.

Therefore, frequency components equal to the natural frequency $\{\Delta=0\}$ are transformed to the constant frequency $\{\omega_{s+\omega n}(t^*)\}$, and components with a given (constant) separation frequency from the natural frequency are transformed in a manner that maintains that separation frequency.

The formulation of Equation (1) above is thus referred to as the "upper sideband formulation" in that the upper sideband created in the modulated signal is stationary for the purposes of identifying the mode of interest. Using a carrier frequency described by:

$$\omega_c(t)=\omega_s+[\omega_n(t)-\omega_n(t^*)]$$

would generate a modulated signal whose lower sideband would have stationary properties for the mode of interest (the "lower sideband formulation"). The first embodiment described below uses the lower sideband formulation whilst the second and third embodiments use the upper sideband formulation.

In situations where $y(t)$ is not sufficiently narrowband, it can be bandpass filtered prior to modulation to prevent interference between signal components which may be transformed into the same frequency range; e.g. a low frequency component f1 in $y(t)$ may be translated up to f2 in the modulated signal but this may coincide with a high frequency component f3 in $y(t)$ which has been translated down and now also appears as f2 in the modulated signal.

Therefore in most cases, the modulated signal will be determined as:

$$y_m(t)=s_c(t).y(FL, FU, t),$$

where y(FL, FU, t) represents the bandpass filtered result after filtering $y(t)$, and FL and FU respectively denote the lower and upper passband frequencies and may be constant or time dependent. FL and FU are generally selected to ensure that frequency components near the mode of interest are unaffected whilst frequencies away from this local region are rejected.

The selected sideband of the modulated signal can now be further processed using standard techniques for stationary data, such as Power Spectral Density (PSD) function computations, to yield information about the modal bandwidth and damping. If further processing is to be done in the frequency domain, then the signal components in the other sideband are ignored. If further processing is to be done in the time domain, then the modulated signal may be bandpass filtered around the components in the sideband of interest prior to any such processing.

If absolute, rather than relative, magnitude values are important, the modulated signal can be multiplied by a factor of two to correctly scale the levels.

In situations where the input $x(t)$ is known, then this may also be modulated in a similar fashion to the response $y(t)$. Thus a modulated input signal $x_m(t)=s_c(t).x(t)$ is formed. As with the response signal $y(t)$, the input signal $x(t)$ may be bandpass filtered first to make it sufficiently narrowband. The two modulated signals (input and output) may then be used, for example to compute the frequency response function between the signals, using standard spectral and cross-spectral techniques as a precursor to mode and damping estimation.

The above processes may be carried out in an analogue or a digital manner. Multiple inputs and/or outputs may be processed using the above methodology.

If the excitation is also non-stationary so that the time average force level varies significantly, then this may also be compensated for if required. Generally the excitation changes have a time constant that is much longer than any considered vibration time constants (i.e. the changes are slow in comparison to the vibration itself. One approach is to track the mode of interest and compute a smooth running root-mean-square (rms) profile, a(t), of the response. This may then be used to normalise the modulated signal prior to any standard analysis. The signal is thus made stationary as either the upper or lower sideband part of $\{[s_c(t).y(FL, FU, t)]/[a(t)]\}$, depending on the formulation used.

In small time regions where the modal frequency of the mode of interest coincides with other modal frequencies, the transformed data may be ignored if necessary prior to performing any standard stationary data analysis.

As the natural frequency of the non-stationary sideband will vary to a greater extent after processing as described above, it is possible that data from the two sidebands overlaps at some point in time. This is generally undesirable since such an overlap can affect the analysis of the stationary sideband.

Therefore it is preferable that the carrier signal is chosen so that such an overlap does not occur in the period of interest. This can be achieved by choosing a carrier frequency which is greater than the difference between the highest and lowest values of the natural frequency of said mode over the period of interest, as shown below. The analysis below is based on positive values of the carrier signal frequency $\omega_s$, although negative values are possible, and the same considerations would apply, but with the "upper" and "lower" sidebands being reversed.

Figure 28:
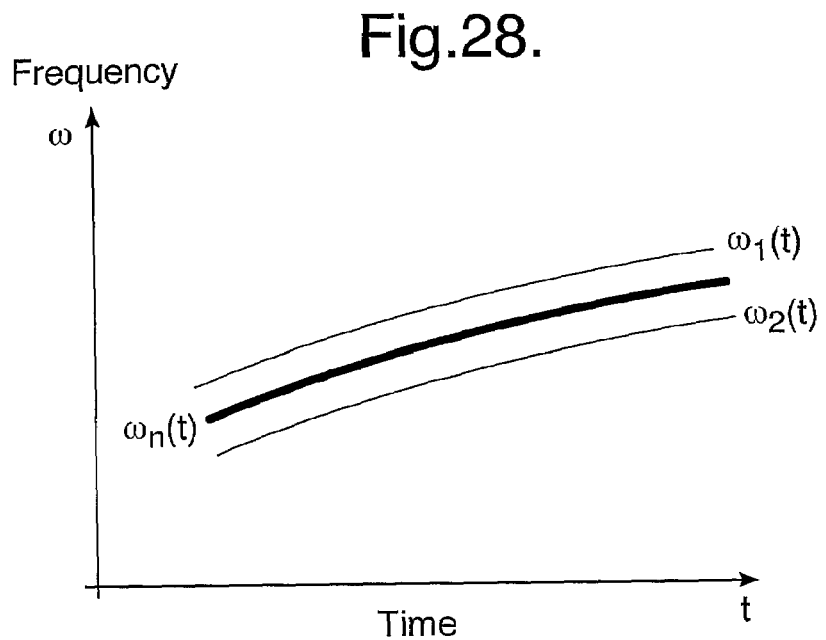
FIGS. 28 and 29 show schematic zmod plots of data respectively prior to and after processing in order to illustrate an aspect of the theory.
Figure 29:
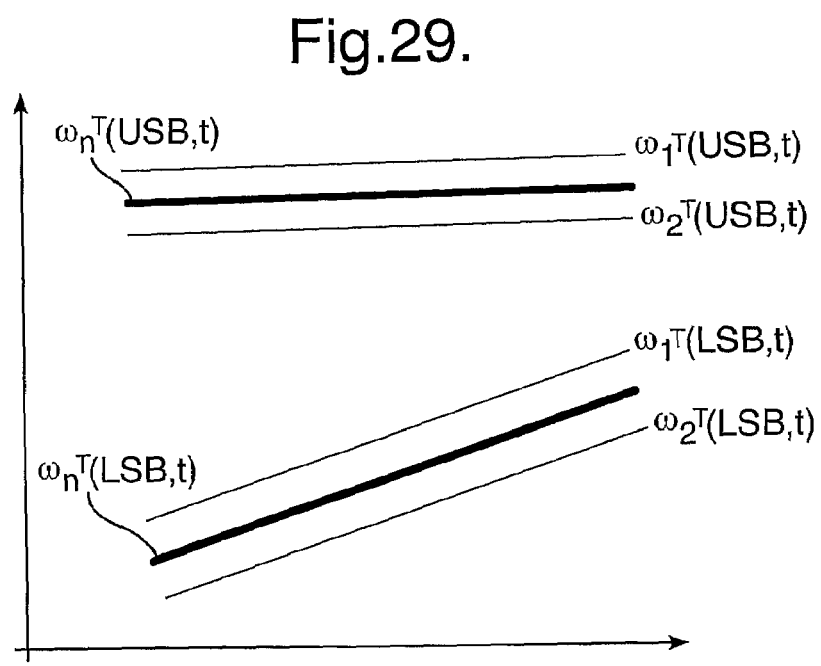

The zmod plots of the response of a fictional system with a single mode whose natural frequency changes, and which is subject to random excitation are shown in FIGS. 28 and 29 which respectively show the data before and after processing according to an embodiment of the present invention.

The illustrated transformation achieved by the processing of this embodiment can be considered a "good" transformation in the context of achieving separation of the upper and lower sidebands by appropriate selection of $\omega_s$, such that the upper sideband (USB) frequencies are separated from the lower sideband (LSB) frequencies over at least a significant portion of the time history, and preferably over the entire period of interest.

To determine the values of $\omega_s$ which may allow such "good" transformation, we consider the two frequency profiles:

profile 1: $\omega_1(t)=\omega_n(t)+\delta$ profile 2: $\omega_2(t)=\omega_n(t)-\delta$, where $\omega_n(t)$ describes how the natural frequency varies, and $\delta$ represents the maximum frequency separation from the natural frequency which may be of interest. Typically, $\Delta$ will be of the order of the modal bandwidth.

Under the transformation of embodiments of the invention $\omega_1(t)$ gets transformed to $\omega_1^T(USB,t)$ and $\omega_1^T(LSB,t)$; and $\omega_2(t)$ is similarly transformed. Using the superscript 'T' to represent the transformed data, we will therefore have the following profiles associated with the transformed data:

profile 3: $\omega_1^T(USB, t) = \omega_1(t) + \omega_c(t)$ profile 4: $\omega_1^T(LSB, t) = \omega_1(t) + \omega_c(t)$
$= \omega_n(t) + \delta - \omega_c(t)$ (after substitution from above)

profile 5: $\omega_2^T(USB, t) = \omega_2(t) + \omega_c(t)$
$= \omega_n(t) - \delta + \omega_c(t)$ (after substitution from above)

profile 6: $\omega_2^T(LSB,t)=\omega_2(t)-\omega_c(t)$, where USB & LSB refer respectively to the upper and lower sidebands.

If required, the data may be initially filtered (prior to the transformation) to ensure that the signal only has significant frequency components in the approximate range $\omega_n(t)+/-\delta$.

Imposing a requirement that the USB & LSB frequencies are separated (i.e. do not mix) over the entire period of interest or time history implies that:

$\omega_2^T(USB,t) > \omega_1^T(LSB,t)$ for all $t$.

By making all the relevant substitutions for $\omega_2^T(USB,t)$ and $\omega_1^T(LSB,t)$ from above, we obtain the condition that:

$\omega_n(t)-\delta+\omega_c(t) > \omega_n(t)+\delta-\omega_c(t)$, and therefore that:

$\omega_c(t)>\delta$.

Substituting from Equation (1) gives:

$\omega_s>\delta+[\omega_n(t)-\omega_n(t^*)]$

Denoting the maximum and minimum values of $\omega_n(t)$ respectively by $\omega_{n,max}$ and $\omega_{n,min}$, the above preferred constraint equation on $\omega_s$ may be conservatively and further simplified to:

$\omega_s>\delta+[\omega_{n,max}-\omega_n(t^*)]$ and thence to $\omega_s>\delta+[\omega_{n,max}-\omega_{n,min}]$ which are sufficient conditions.

In cases where the signal bandwidth (due to significant natural frequency changes) is much larger than the modal bandwidth, i.e. where $[W_{n,max}-W_{n,min}] >> \delta$, the constraint equation approximately simplifies further to:

$\omega_s>\delta[\omega_{n,max}-\omega_{n,min}]$

Therefore selecting $\omega_s$ to be greater than the difference between the highest and lowest natural frequency for the mode of interest is sufficient to ensure that the lower and upper sidebands are sufficiently separated. Clearly setting $\omega_s>\omega_{n,max}$ also satisfies the condition.

Even if this most stringent condition is not met, the transformation effected by embodiments of the invention may still be useful as there will normally be parts of the data time history which reveal useful information.

A similar construction can be done for the Engine Order situations. Again we consider an upper sideband formulation and use similar reasoning and notation to that above.

Setting $\omega_n(t^*)=0$, then $\omega_c(t)=\omega_s-\omega_n(t)$.

Consider the transformation of the engine order frequency $(\omega_{eo})$:

$\omega_{eo}^T(USB, t) = \omega_{eo}(t) + \omega_c(t)$
$= \omega_{eo}(t) + \omega_s - \omega_n(t)$ $\omega_{eo}^T(LSB, t) = \omega_{eo}(t) - \omega_c(t)$
$= \omega_{eo}(t) - \omega_s + \omega_n(t)$ The condition for $\omega_s$ is $\omega_{eo}^T(USB,t) > \omega_{oe}^T(LSB,t)$ Therefore we obtain:

$\omega_{eo}(t)+\omega_s-\omega_n(t)>\omega_{eo}(t)-\omega_s+\omega_n(t)$ and $\omega_s>\omega_n(t)$ Again $\omega_s>\omega_{n,max}$ would of course be conservative and satisfy the condition.

First Embodiment

A modelled scenario is used to illustrate a method according to a first embodiment of the present invention.

A model system is subjected to random vibration excitation. The model system has two dominant modes, both of which are time-varying, that create a typical response, as shown in FIG. 1. In a real situation, this response could be, for example, a strain or acceleration measurement from a mechanical system such as a gas turbine engine or a component thereof.

The simulation is conducted over a period of 100 seconds with a time interval between discrete points of the simulation of 1/5000 seconds.

The two modes have the following characteristics:

The natural frequency of Mode 1 varies from 100 Hz to 110 Hz between 0 and 80 seconds and then remains constant. Mode 1 has Q=100, Q being the quality factor which can be calculated as the characteristic or natural frequency divided by the modal bandwidth.

The natural frequency of Mode 2 varies from 200 Hz to 250 Hz between 0 and 80 seconds and then remains constant. Mode 2 has Q=50.

The −3 dB modal bandwidths associated with these modes are approximately 1 Hz and 4.5 Hz respectively.

Figure 2:
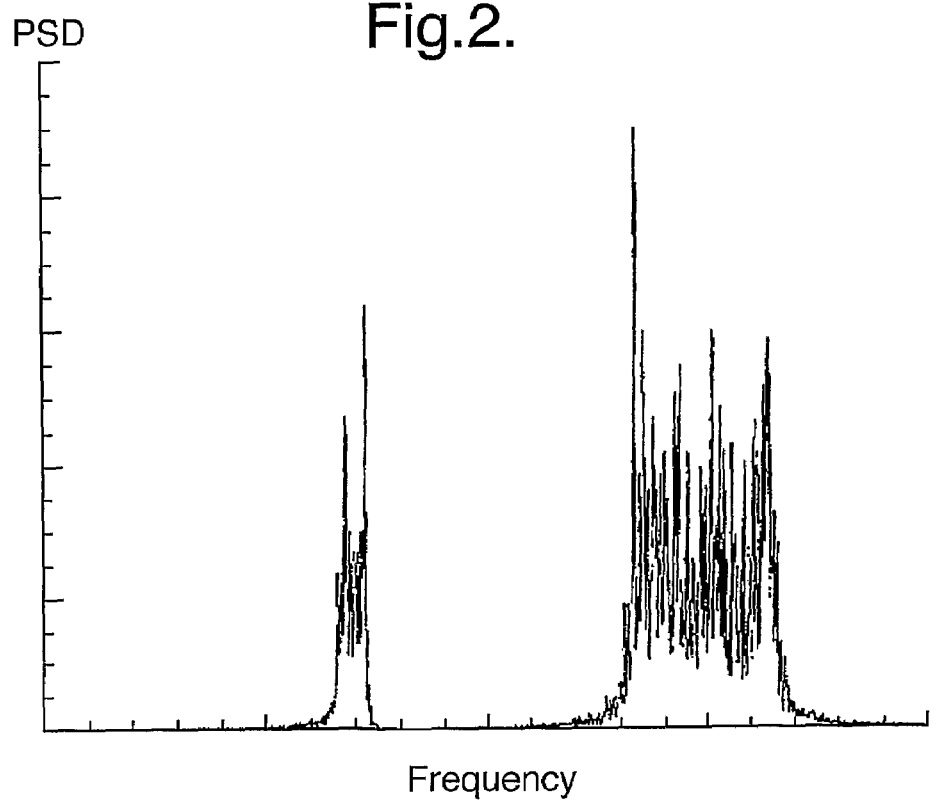
FIG. 2 shows a power spectral density (PSD) computation of the response of FIG. 1.

The system response is very clearly non-stationary as a result of the large changes in natural frequency. The PSD computation of the whole period of analysis in FIG. 2 shows the smearing of the frequencies due to this non-stationary behaviour. The frequency resolution of this analysis is approximately 0.1562 Hz.

Figure 3:
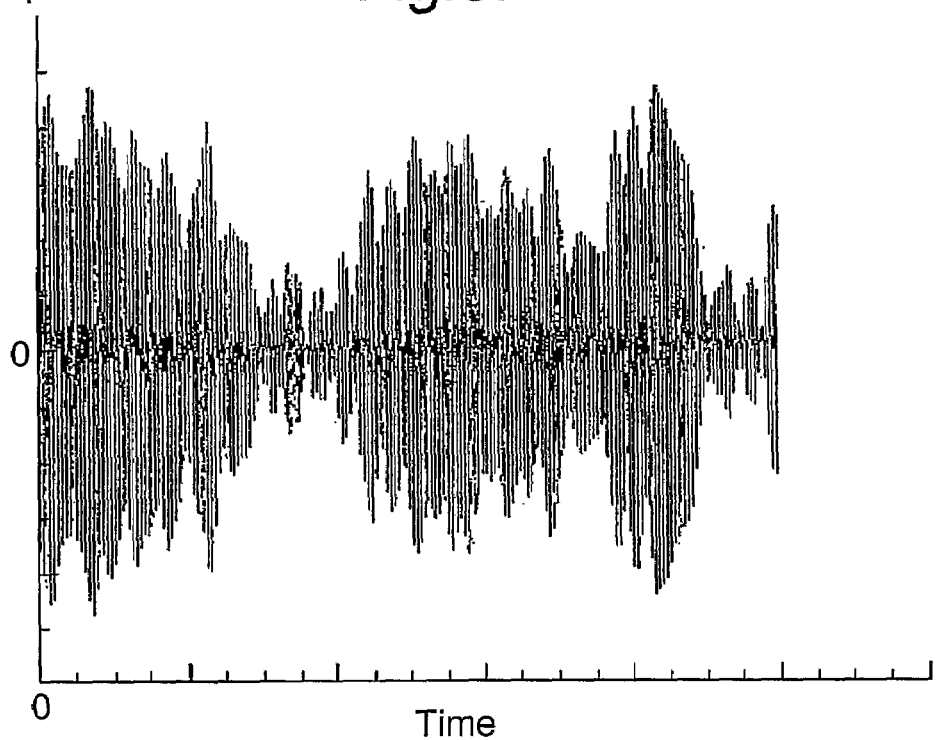
FIG. 3 shows the response of FIG. 1 which has been bandpass filtered around a mode of interest.
Figure 4:
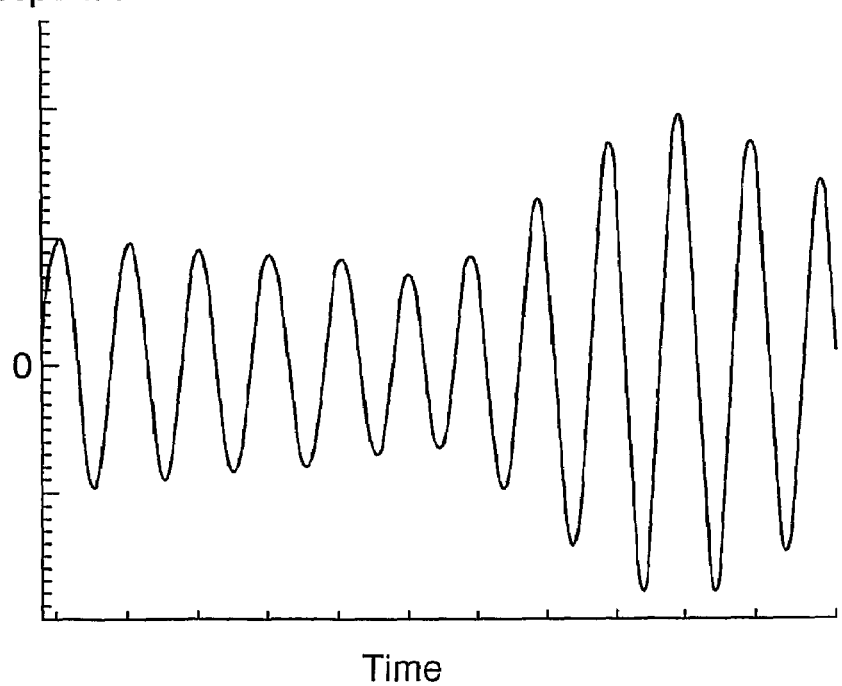
FIG. 4 shows an expanded part of the response of FIG. 3.

To estimate the variation of the natural frequency of Mode 1, the system response is preferably bandpass filtered (e.g. between 50-150 Hz) to obtain principally the contribution of Mode 1 to the response. This filtered response is shown in FIG. 3 and a part of it is shown in magnified form in FIG. 4.

This filtered response may be analysed to compute the "instantaneous" frequency and its variation over the time of the response. This analysis may be done by computing the time between successive zero-point crossings, which are taken to represent half periods of the response.

Figure 5A:
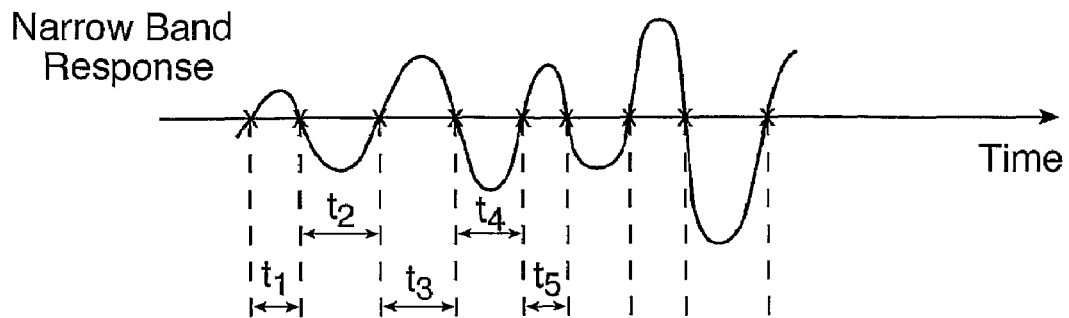
FIGS. 5a-5c show schematic representations of, respectively, a magnification of the narrowband response, a data set of signal zero crossing separation times of that response, and a data set of instantaneous frequencies of that response.
Figure 5B:
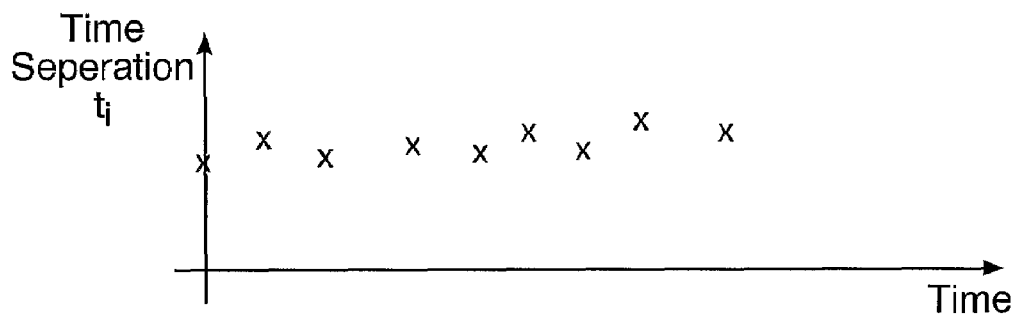
Figure 5C:
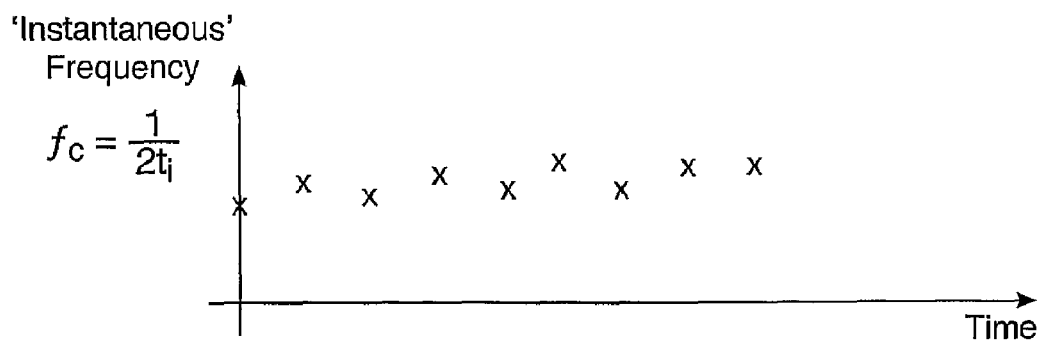

FIG. 5a shows a schematic magnification of a narrowband response, showing the zero crossing points. From the zero crossing points, a time-varying data set of separations can be obtained, as shown in FIG. 5b. This can be translated to a time-varying data set of instantaneous frequencies ($f_i=\frac{1}{2}t_i$) as shown in FIG. 5c. Note that the perturbations within the small time sample shown are generally not significant enough to be noticeable on the overall plot of the time separation or instantaneous frequency.

Alternatively, local curve fitting analysis can be used to compute the "instantaneous" frequency and its variation. For example a sinusoidal function (in the interval [0, π] which describes a half cycle) may be fitted to all data points between consecutive zero-crossing points. This fitting is repeated for all points to give the frequency profile.

Figure 6:
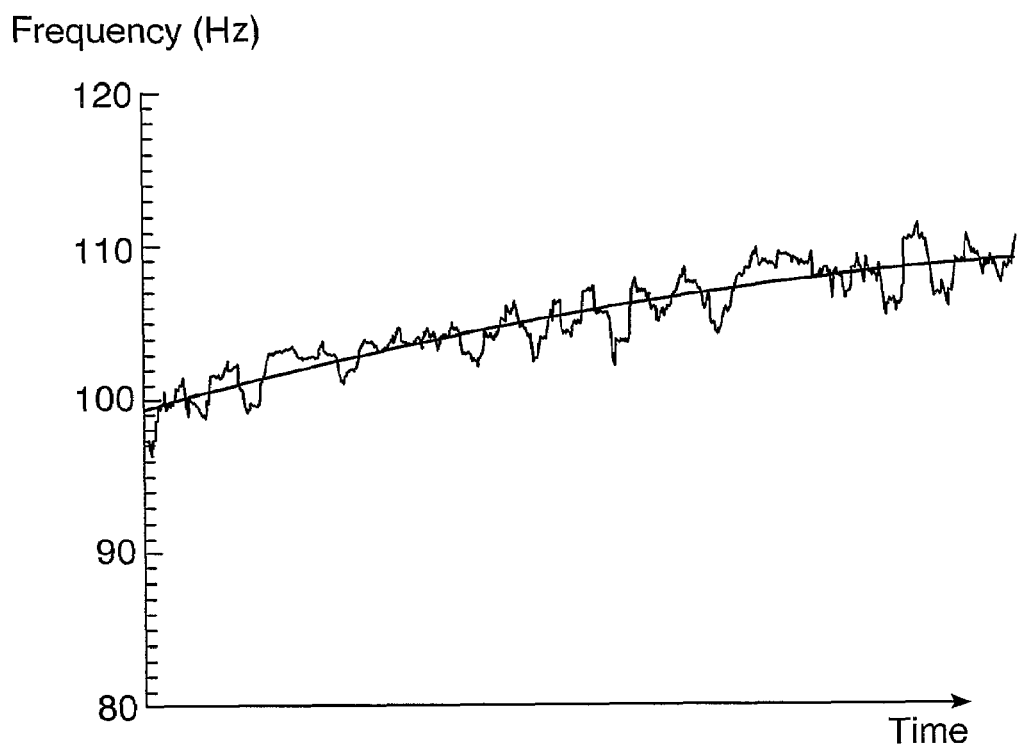
FIG. 6 shows the instantaneous frequency of the response over the period of analysis.

The frequency data may itself be filtered. A running average of the instantaneous frequency or a curve fitting process may then be used to estimate the variation of the natural frequency of the mode over the period of the response. FIG. 6 shows a plot of the variation of the instantaneous frequency (jagged line) and of the smoothed frequency (obtained using curve fitting) with respect to time.

Alternatively an estimate of the natural frequency variation could be obtained by analysis of a waterfall type spectral analysis of the whole response signal as shown in the second embodiment below.

Next, a shift frequency of, in this case 50 Hz, is chosen. That is, a carrier signal is generated which has a frequency of 50 Hz more than the change in the smoothed instantaneous frequency of Mode 1 over the course of the response. The magnitude of the shift frequency ensures that the lower and upper sidebands created by the modulation process are well separated.

Figure 7:
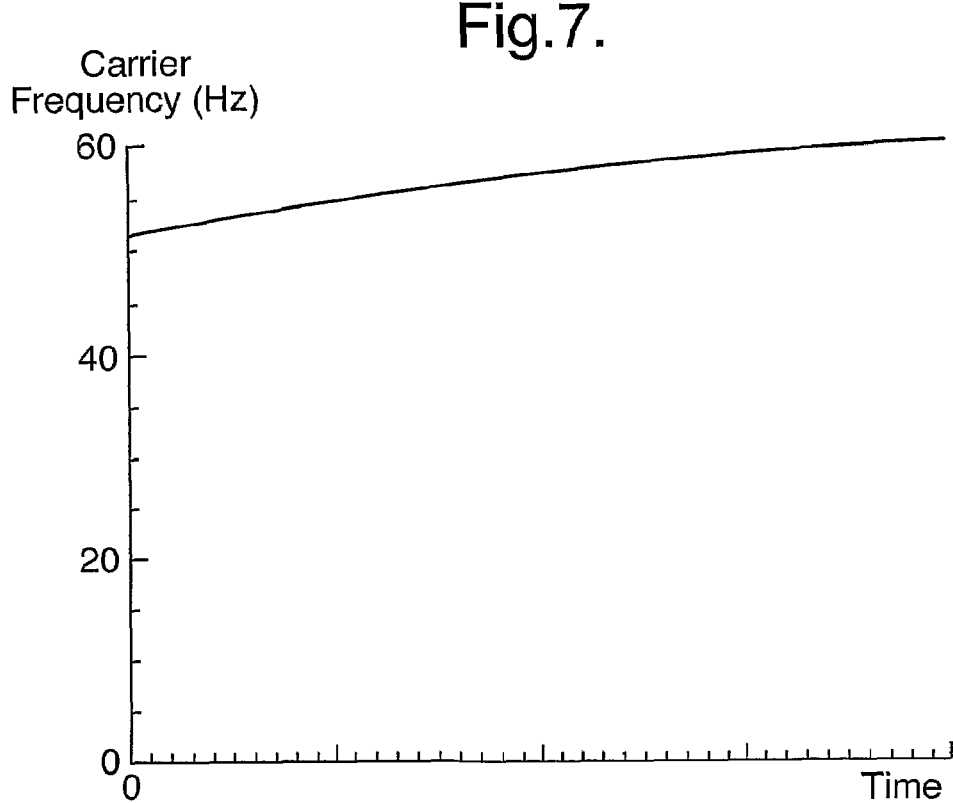
FIG. 7 shows the variation in the carrier frequency used in the method of a first embodiment of the present invention.

The carrier frequency of the first embodiment is formed using the lower sideband formulation described above and is shown in FIG. 7.

The carrier signal thus formed is then multiplied by the narrowband filtered response (shown in FIG. 3).

The resulting signal can then be processed using standard analysis techniques and methods for stationary data sets.

Figure 8:
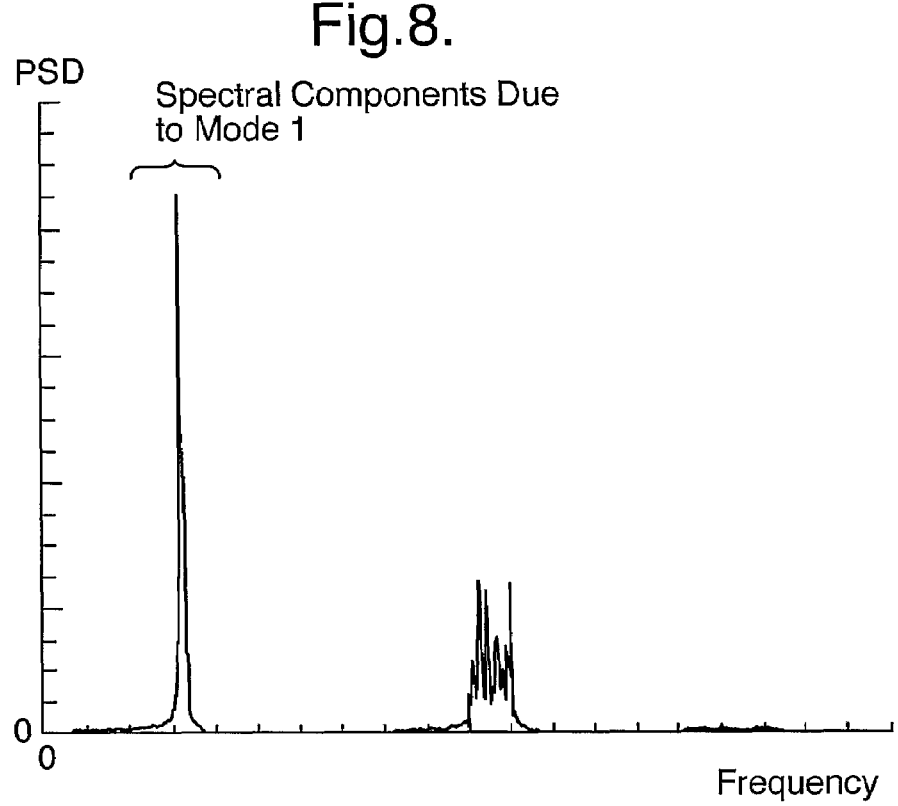
FIG. 8 shows a PSD calculation of the response after the method of an embodiment of the present invention has been used.

For example, the PSD of the resulting modulated signal may be computed, as shown in FIG. 8. The lower frequency sideband indicated represents the spectral distribution associated with Mode 1 after the transformation to the stationary data set and mapping to a lower frequency. The other spectral components are the upper frequency sideband of Mode 1, which have been caused to become even more non-stationary by the processing.

As can be seen from a comparison of the PSD shown in FIG. 8 with that shown in FIG. 2, the signal is much less spread in frequency and therefore can be analysed more easily using standard methods (which need not include determining a PSD function).

Specifically, the response due to mode 1 has been effectively made stationary without energy being distributed over a wide band due to natural frequency changes.

In particular, features such as the vibration level and modal bandwidth and/or damping information of the lower frequency sideband can be much more accurately and easily determined.

Second Embodiment

A second modelled scenario is used to illustrate a method according to a second embodiment of the present invention.

Figure 9:
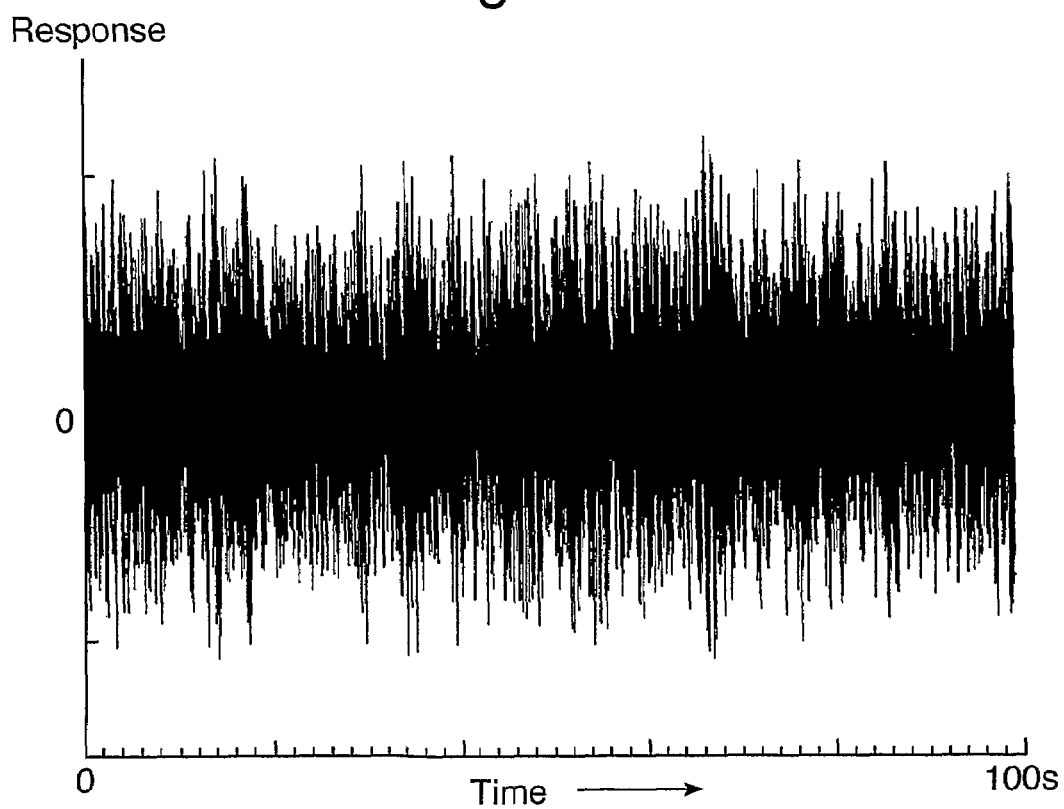
FIG. 9 shows an oscillatory response of a second model system.
Figure 10:
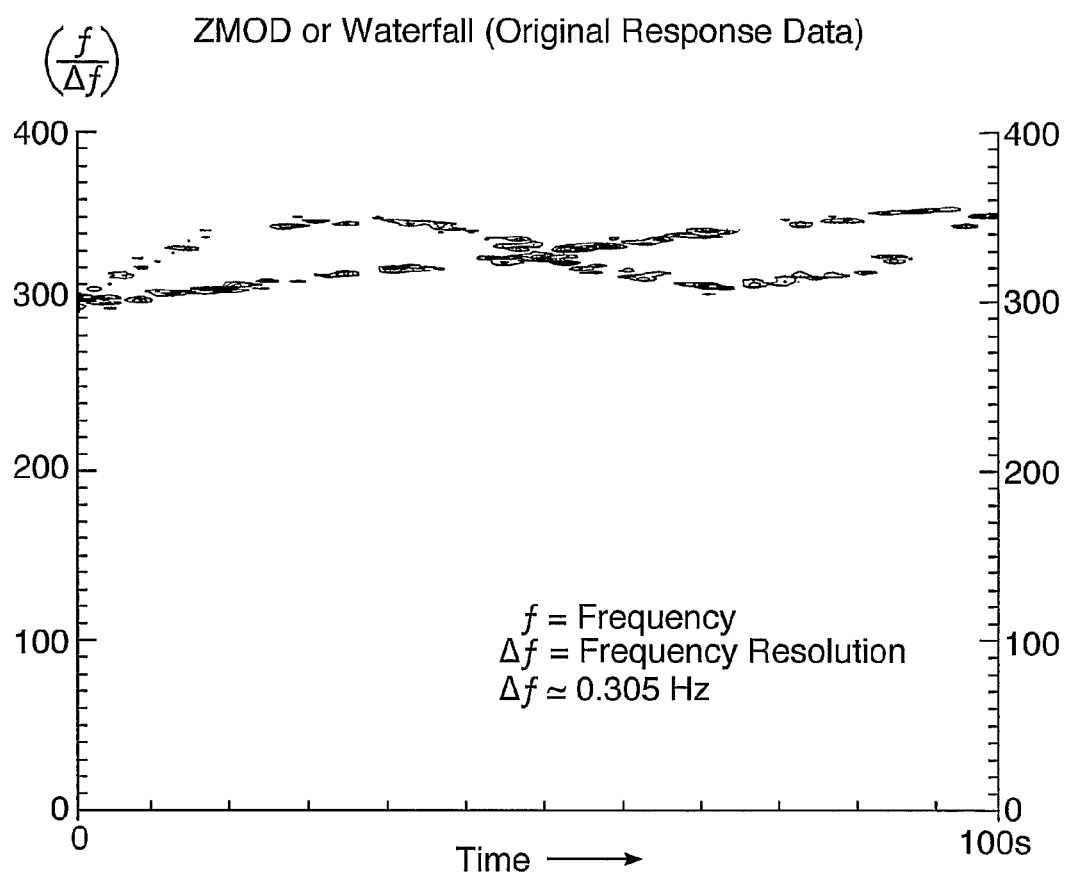
FIG. 10 shows a zmod or waterfall plot of the response of FIG. 9.

A two mode system is excited by random broadband noise. The time history response is shown in FIG. 9. The running spectral profile of this response data, commonly known as the "zmod", waterfall or Campbell diagram, is shown in FIG. 10. Such plots usually plot frequency on the vertical axis, but in the particular plotting program used to produce FIG. 10, the axis represents the non-dimensional parameter of the frequency (f) divided by the frequency resolution (Δf).

The "zmod" or waterfall is obtained from a well known analysis technique which involves splitting the oscillatory data into segments and computing the spectrum associated with each segment. The plot essentially shows how the spectral properties of the data change with time.

Using standard Fourier Transform analysis, the spectra associated with each time segment have a frequency resolution (Δf) which is approximately the inverse of the segment duration.

The model used in this embodiment has two modes. The natural frequency of mode 1 changes linearly with time from 90 Hz at the start of the simulation (t=0) to 110 Hz at the end (t=100 s). The Q level of this mode is 100 which implies a modal bandwidth of approximately 1 Hz.

The digital computer simulation runs over a period of 100 seconds with a time step of 0.0002 seconds. The response data seen is typical of what might be measured from a vibration survey of an engine in which the engine speed is varying.

Mode 2 has a natural frequency which is equal to that of mode 1, plus an oscillatory component. The Q level of this mode is 20. The respective modal root-mean-square (rms) response levels are approximately the same. FIG. 10 illustrates these characteristics.

The objective is to identify the modal bandwidth and damping associated with mode 1.

Figure 11:
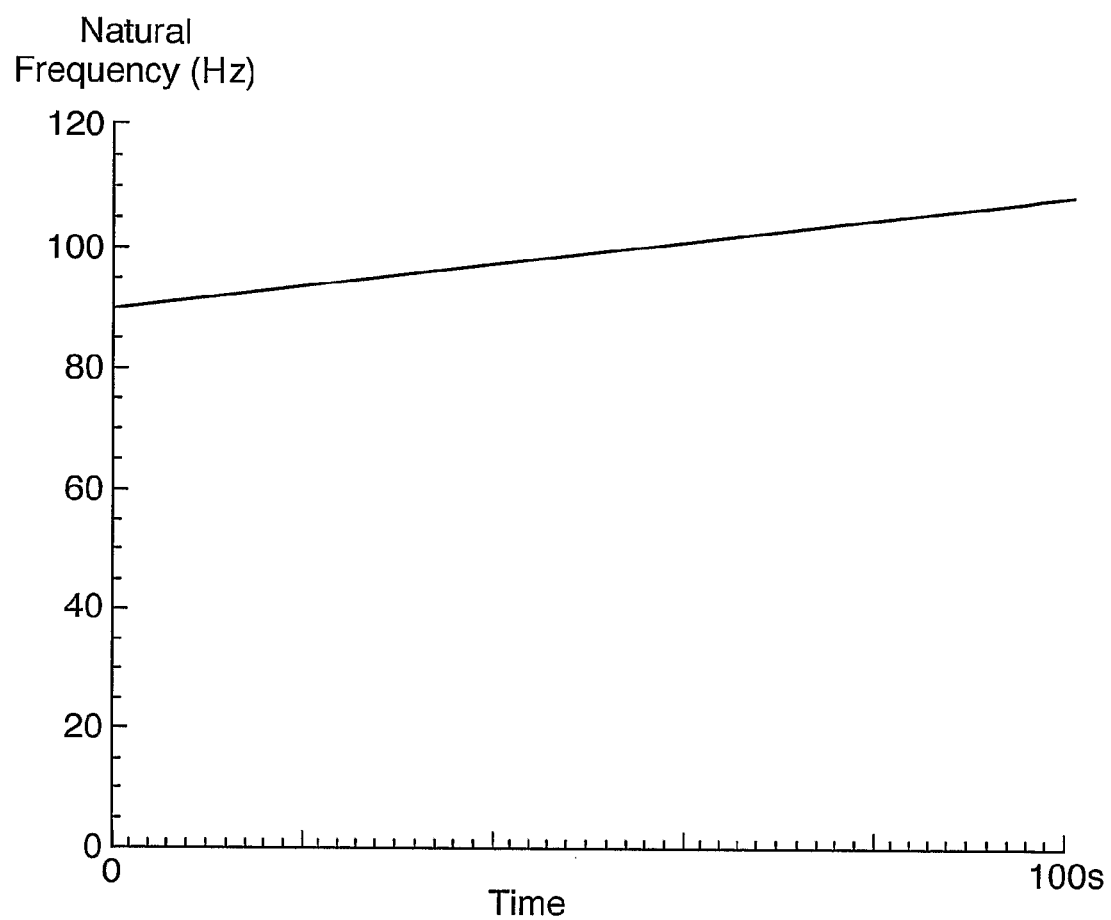
FIG. 11 shows an estimate of the natural frequency of the mode to be identified from the response of FIGS. 9 and 10 over the period of analysis.

In this case the zmod data may be analysed to give an estimate of the natural frequency profile of mode 1, for example by a standard modal curve fitting approach and/or manually cursoring likely estimates prior to conducting a least-squares type fit to the data to determine a smooth frequency profile. This profile is shown in FIG. 11 and is equal to $f_n(t)=\omega_n(t)/2\pi$. The shift frequency is chosen to be 50 Hz; i.e. $\omega_s=2\pi.50$ and t* is chosen to be zero.

Figure 12:
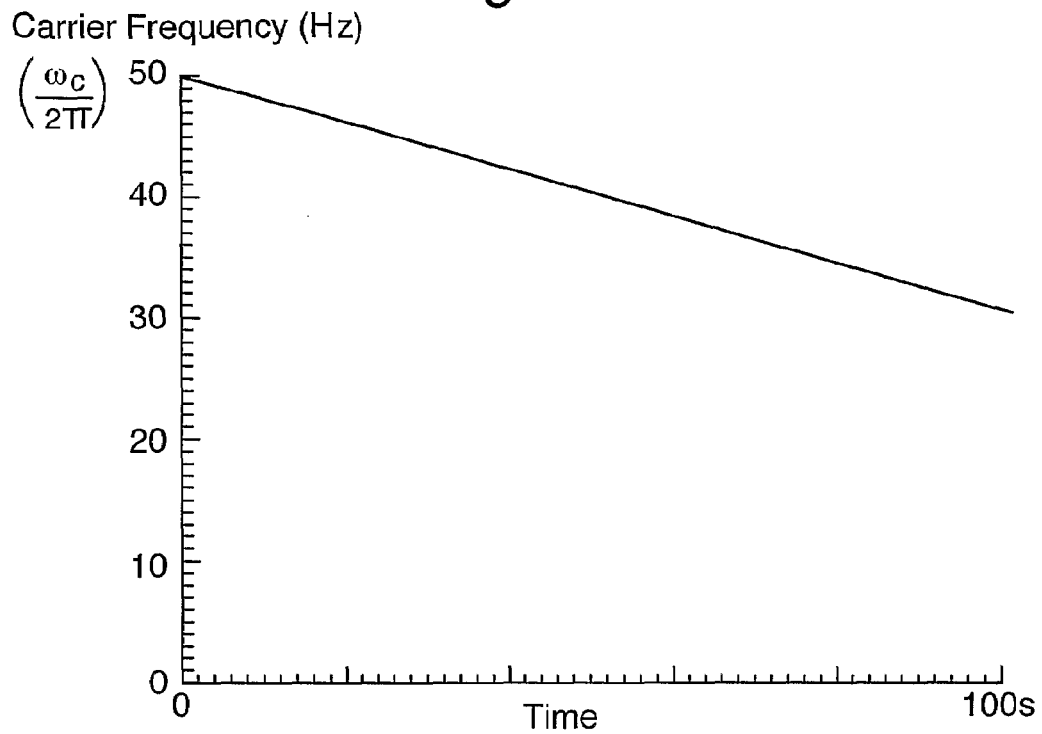
FIG. 12 shows the variation in the carrier frequency used in the method of a second embodiment of the present invention.
Figure 13:
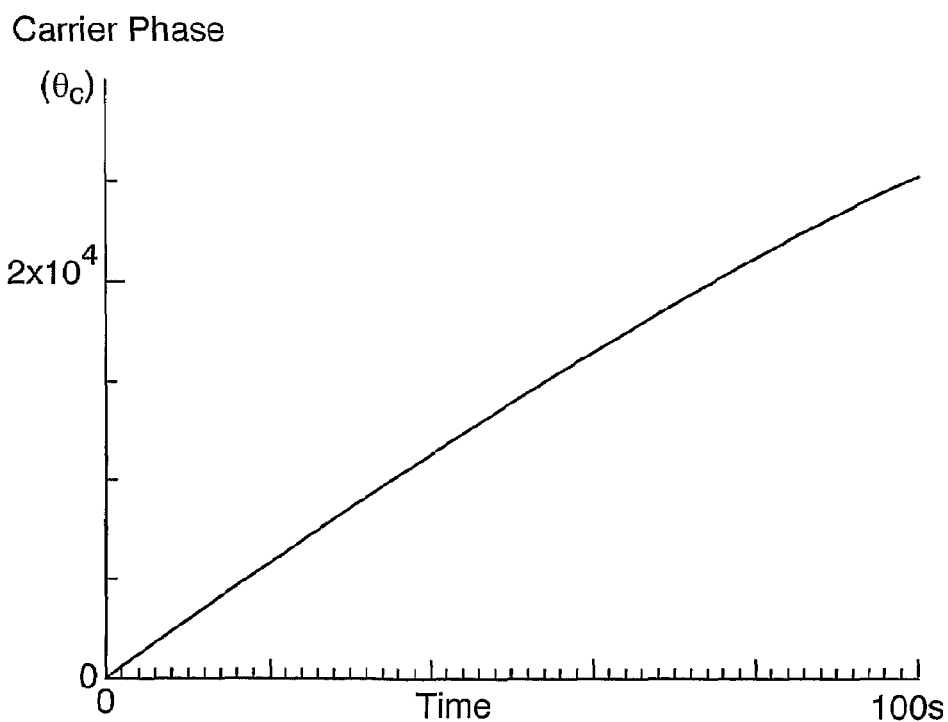
FIG. 13 shows the variation in the carrier phase used in the method of the second embodiment.
Figure 14:
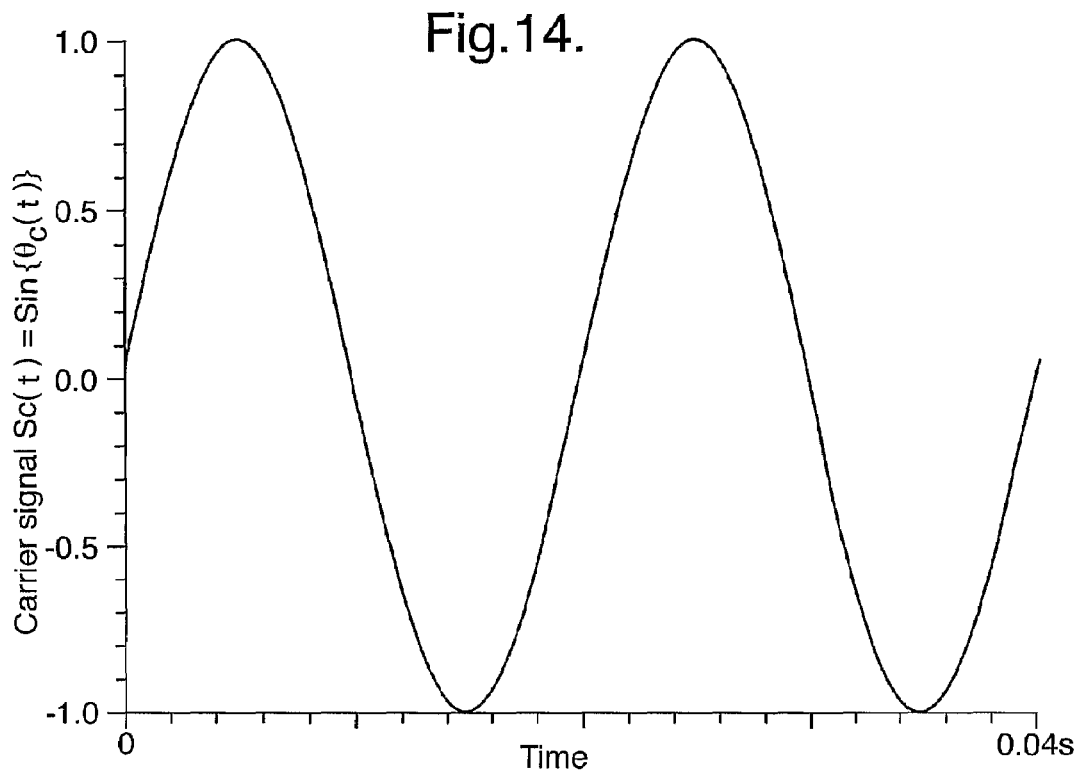
FIGS. 14 and 15 show the carrier signal used in the second embodiment over an interval of 0.04 seconds at respectively the start and end of the simulation period.
Figure 15:
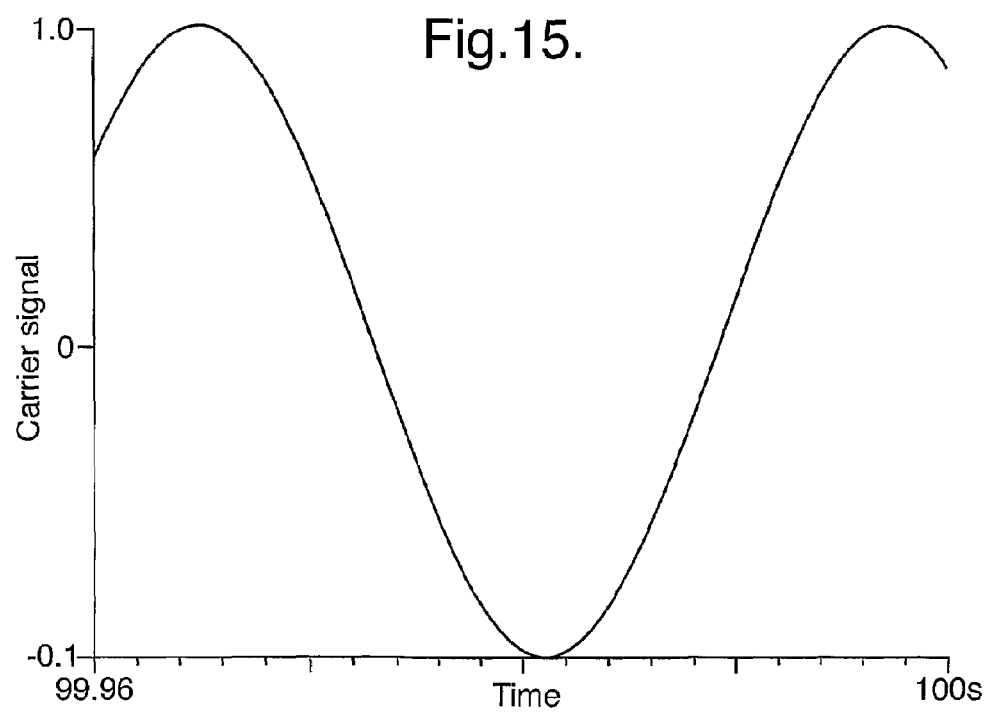

The equations described in the general theory section above are then applied to yield a carrier signal with variable frequency, in this embodiment using the upper sideband formulation. The resulting carrier frequency is shown in FIG. 12. The carrier phase is shown in FIG. 13. FIGS. 14 and 15 show the carrier signal over an interval of 0.04 seconds at the start and end of the simulation respectively.

The response data is bandpass filtered between 80 and 120 Hz and subsequently used to modulate the variable frequency carrier signal computed above.

Figure 16:
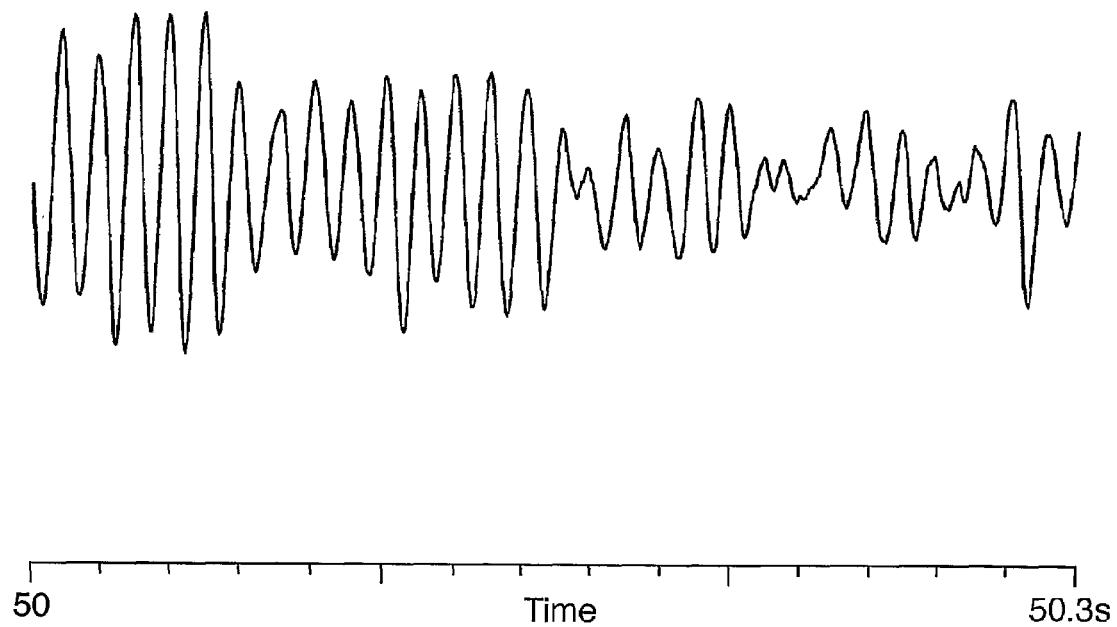
FIGS. 16-19 are expanded plots of the time interval of 50.0 to 50.3 seconds in the second embodiment, showing respectively: the response; the bandpass filtered response; the carrier signal; and the resulting modulated signal.
Figure 17:
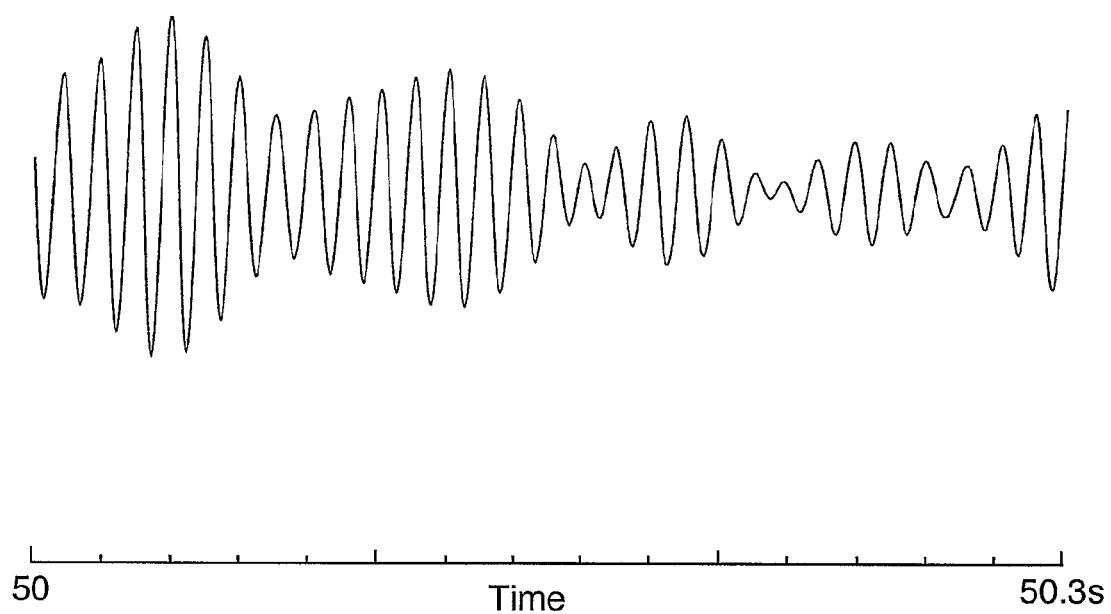
Figure 18:
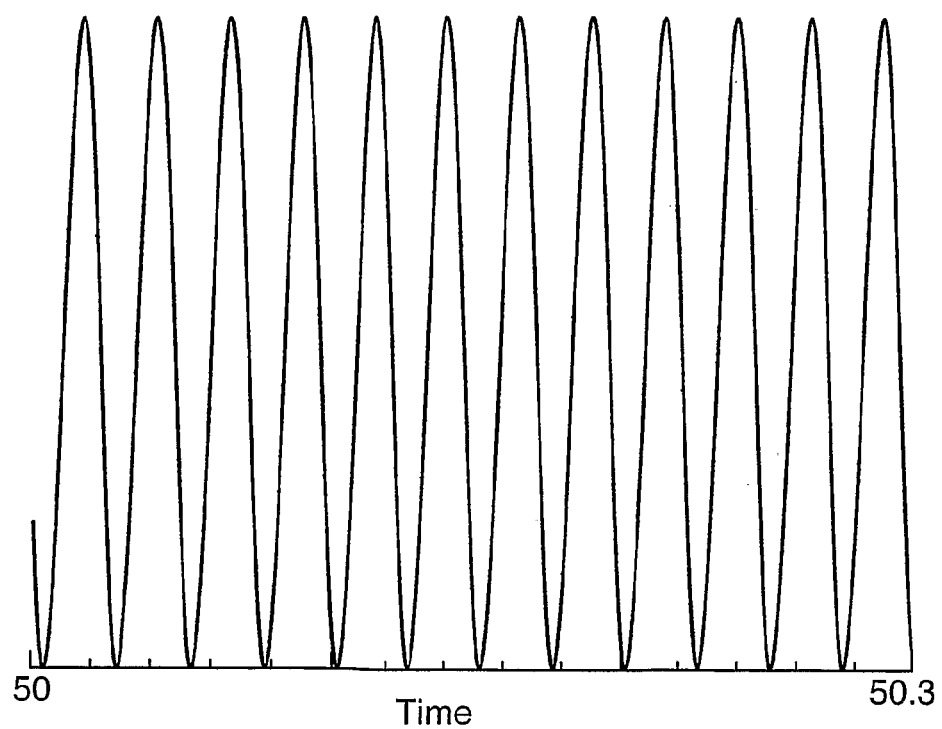
Figure 19:
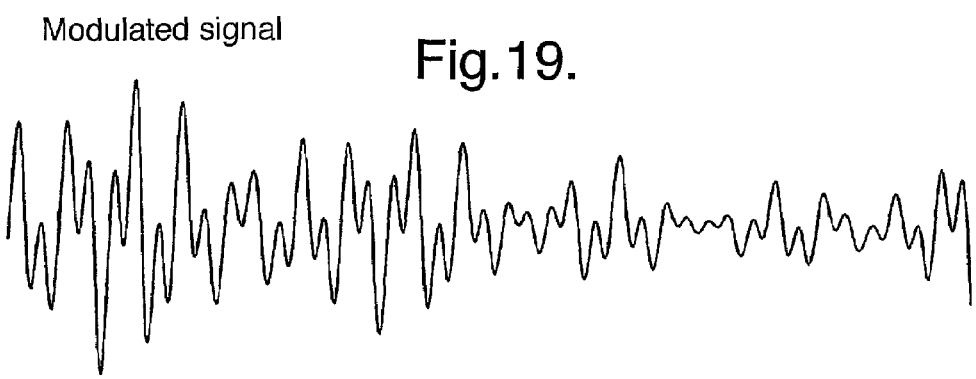

To illustrate this process, various expanded plots of the processed signal are shown over the time interval of 50.0 to 50.3 seconds in FIGS. 16-19. FIG. 16 shows the raw response. FIG. 17 shows the response after it has been bandpass filtered between 80 and 120 Hz. FIG. 18 shows the carrier signal. FIG. 19 shows the modulated signal resulting from multiplying the bandpass filtered response (FIG. 17) and the carrier signal (FIG. 18).

Figure 20:
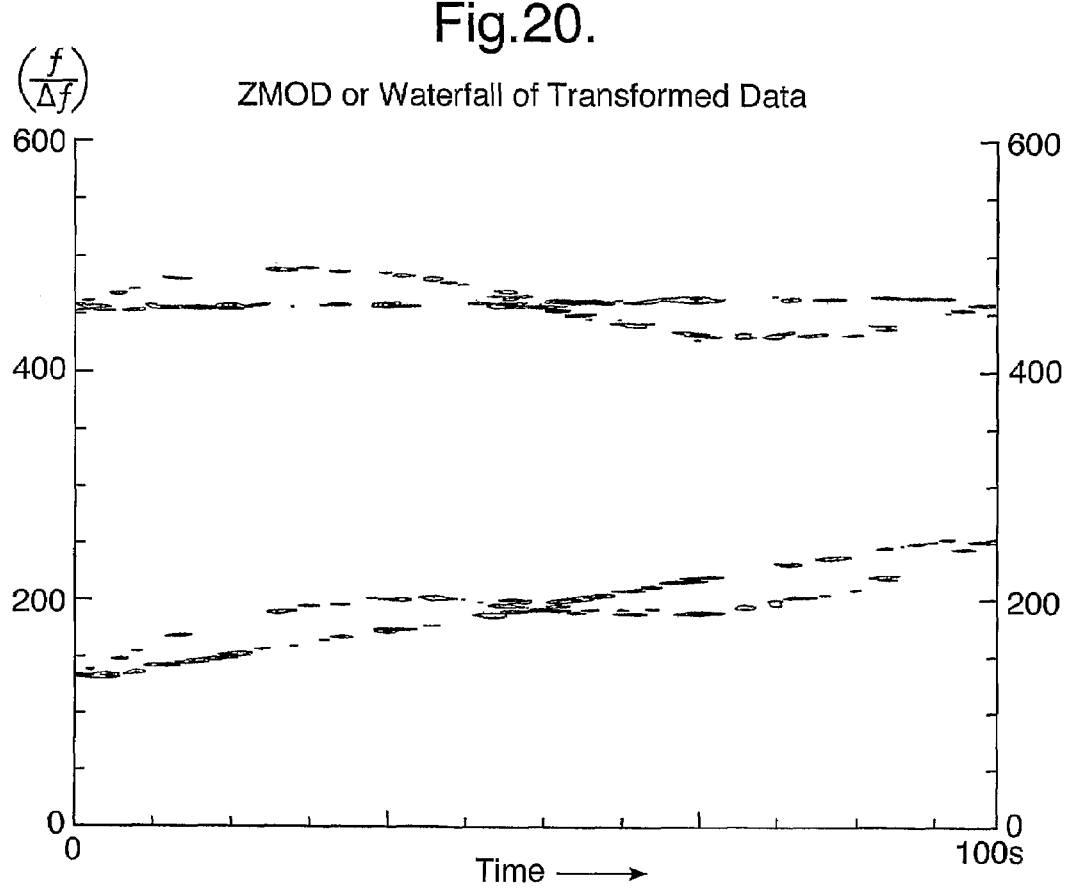
FIG. 20 shows the zmod plot of the resulting modulated signal produced by the second embodiment.

The zmod plot of the resulting modulated signal is shown in FIG. 20, showing both upper and lower sideband data. As can be seen in FIG. 20, the upper sideband data now appears stationary with a constant frequency of 140 Hz in so far as mode 1 is concerned. The mode 2 still has a natural frequency which oscillates around that of mode 1.

If mode 2 had had a natural frequency profile which was simply offset by a constant amount from that of mode 1, then the transformed data would have effectively made stationary both modes.

Figure 21:
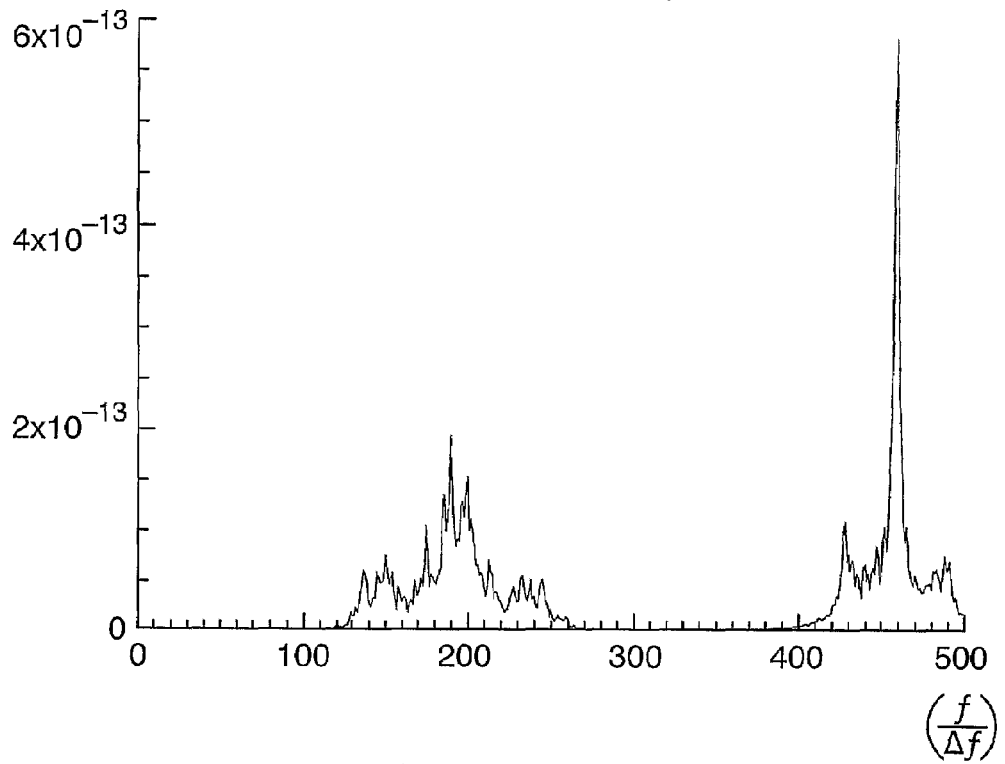
FIG. 21 shows a PSD calculation of the response after the method of the second embodiment has been used.

The transformed data may now be processed using standard techniques as discussed in relation to the first embodiment above. For example, the PSD may be computed as shown in FIG. 21. Further analysis of this PSD demonstrated a correct estimation of the modal damping implicit within the model being simulated.

Figure 22:
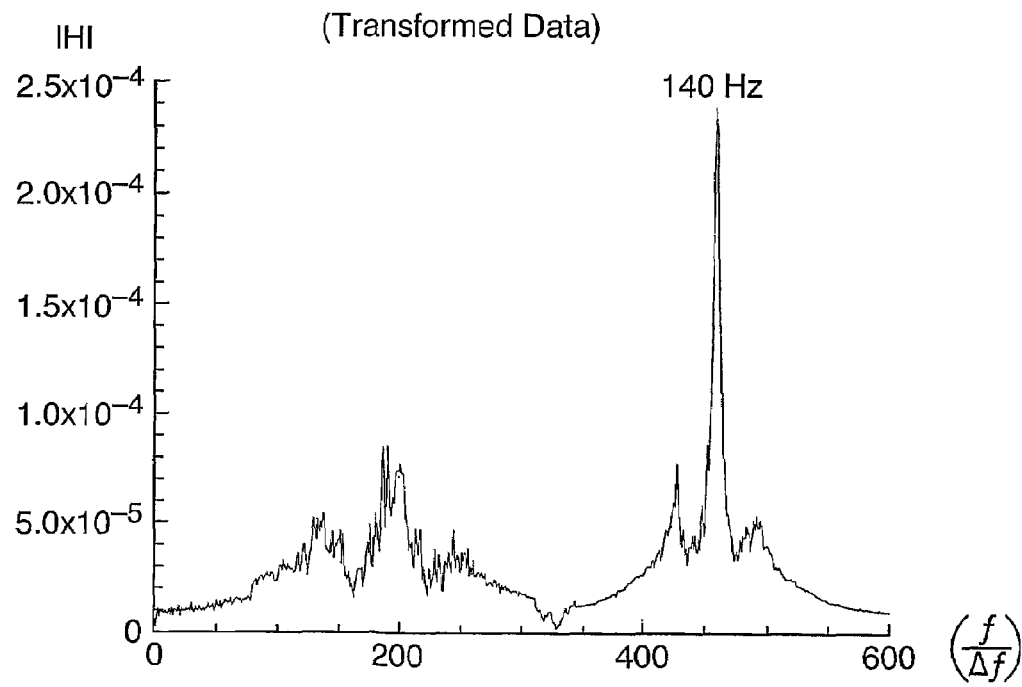
FIGS. 22 and 23 respectively show the magnitude and phase of the frequency response function resulting from the processing of the second embodiment.
Figure 23:
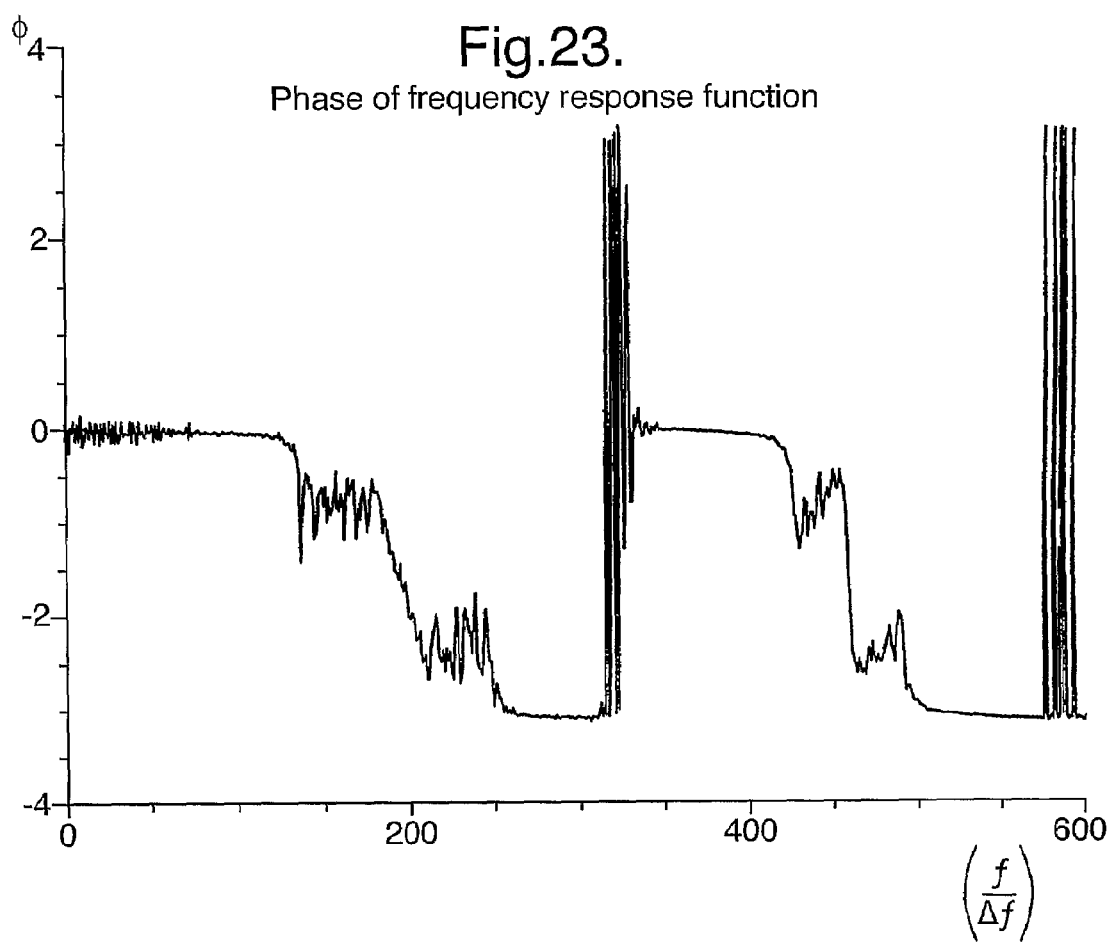

If the excitation force is also known (or measured), as is the case in this example, then it too may be processed by the method of the present invention to generate a modulated signal of the bandpass filtered force. A standard cross-spectral based analysis between the respectively modulated force and response signals will yield frequency response function data around the mode which has been made stationary and whose modal frequency now appears at 140 Hz (90 Hz initial natural frequency of Mode 1+50 Hz shift frequency). This frequency response function data contains both magnitude and phase data which aids the accurate determination of the modal bandwidth and damping. The magnitude and phase of the frequency response function resulting from processing this data are shown in FIGS. 22 and 23 respectively.

Third Embodiment

A third embodiment of the present invention is described in relation to an engine order excitation. Again the upper sideband formulation is used here.

Figure 24:
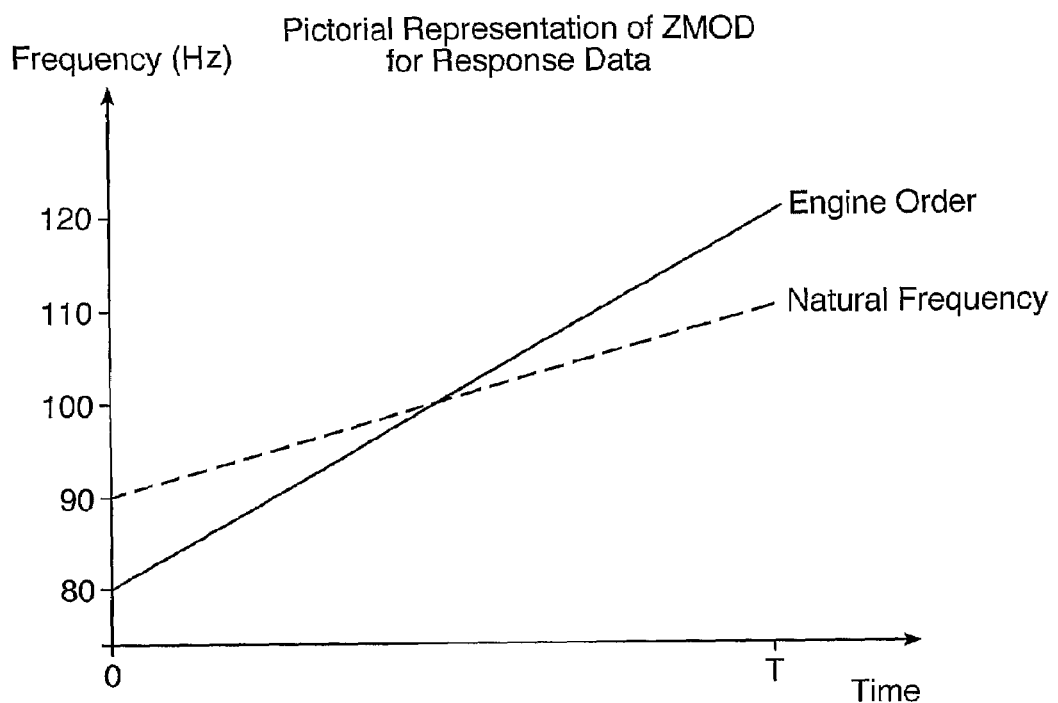
FIG. 24 shows schematically the zmod or waterfall plot of the response data used in a third embodiment of the present invention.

A digital simulation is made of an engine order (EO) traversing a mode whose natural frequency is also varying with time. The zmod or waterfall associated with the resulting response data is shown schematically in FIG. 24. The variation of the modal frequency is also shown to illustrate what would be seen in reality due to low level random (asynchronous) excitation superimposed on the engine order excitation. The modal frequency varies linearly over the period of interest from 90 to 110 Hz. The model mode bandwidth is 1 Hz (i.e. associated Q=100). The EO frequency varies linearly from 80 to 120 Hz over the same time interval.

Figure 25:
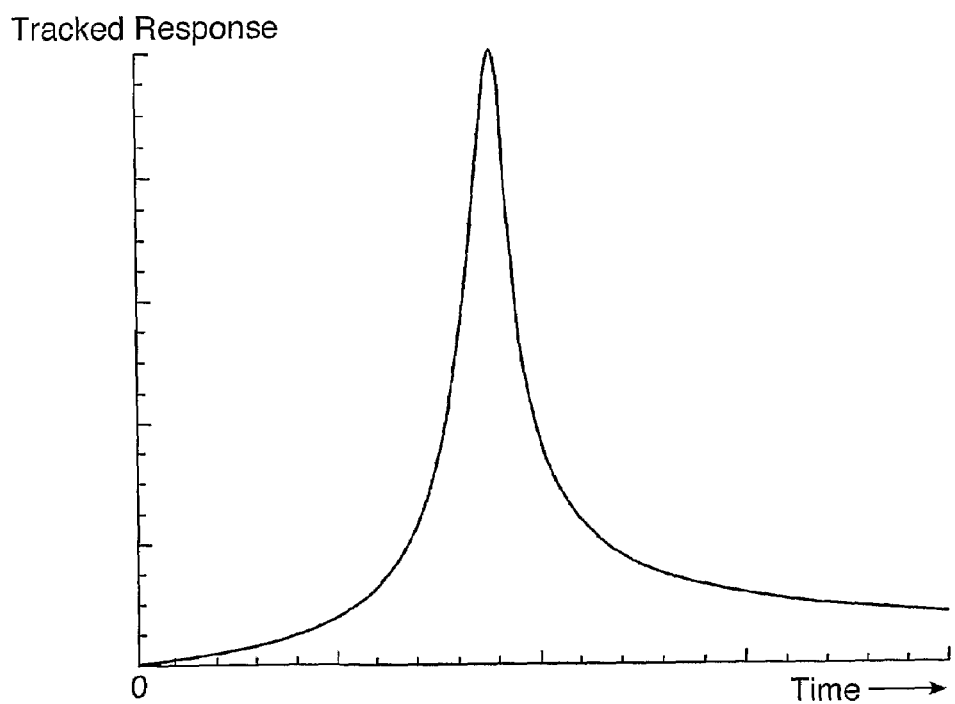
FIG. 25 shows the forced response amplitude profile for the simulation used for the third embodiment.

The forced response due to the engine order is determined by some form of tracking which determines the response at or near EO frequencies. The response amplitude profile for this simulation is shown in FIG. 25. Analysis of this response profile to determine the −3 dB modal bandwidth (related to the damping) yields a value of 1.9 Hz which is almost twice the true value. This error arises due to the natural frequency variation with time, which causes the response profile to distort relative to what would have resulted had the modal frequency remained constant.

From the zmod plot, the natural frequency time profile may be estimated and a variable frequency carrier signal determined as described above. The response is bandpass filtered around the EO frequencies and the resulting signal is modulated with the carrier signal as before. The resulting modulated signal is bandpass filtered around the upper sideband frequencies of the modulated signal.

Figure 26:
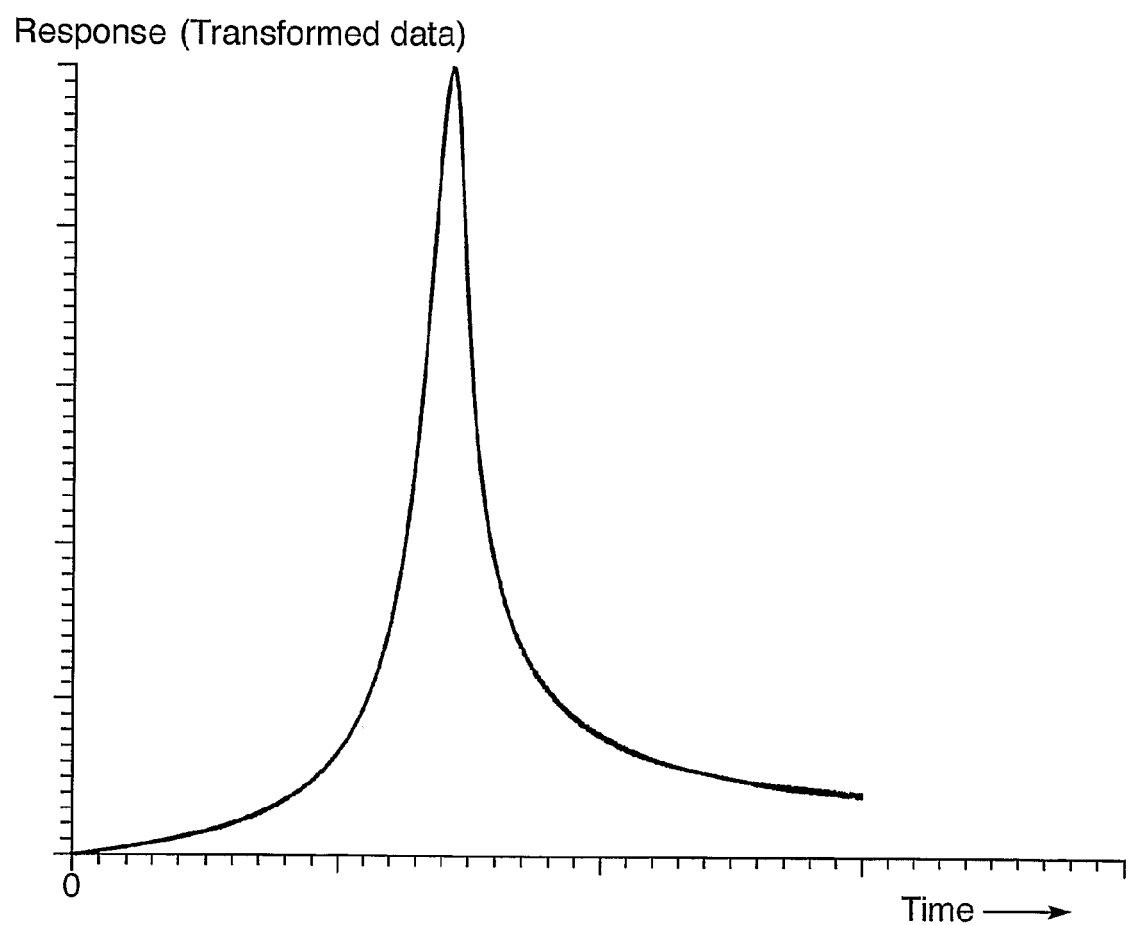
FIG. 26 shows the response amplitude profile after a method according to the third embodiment of the present invention has been used.
Figure 27:
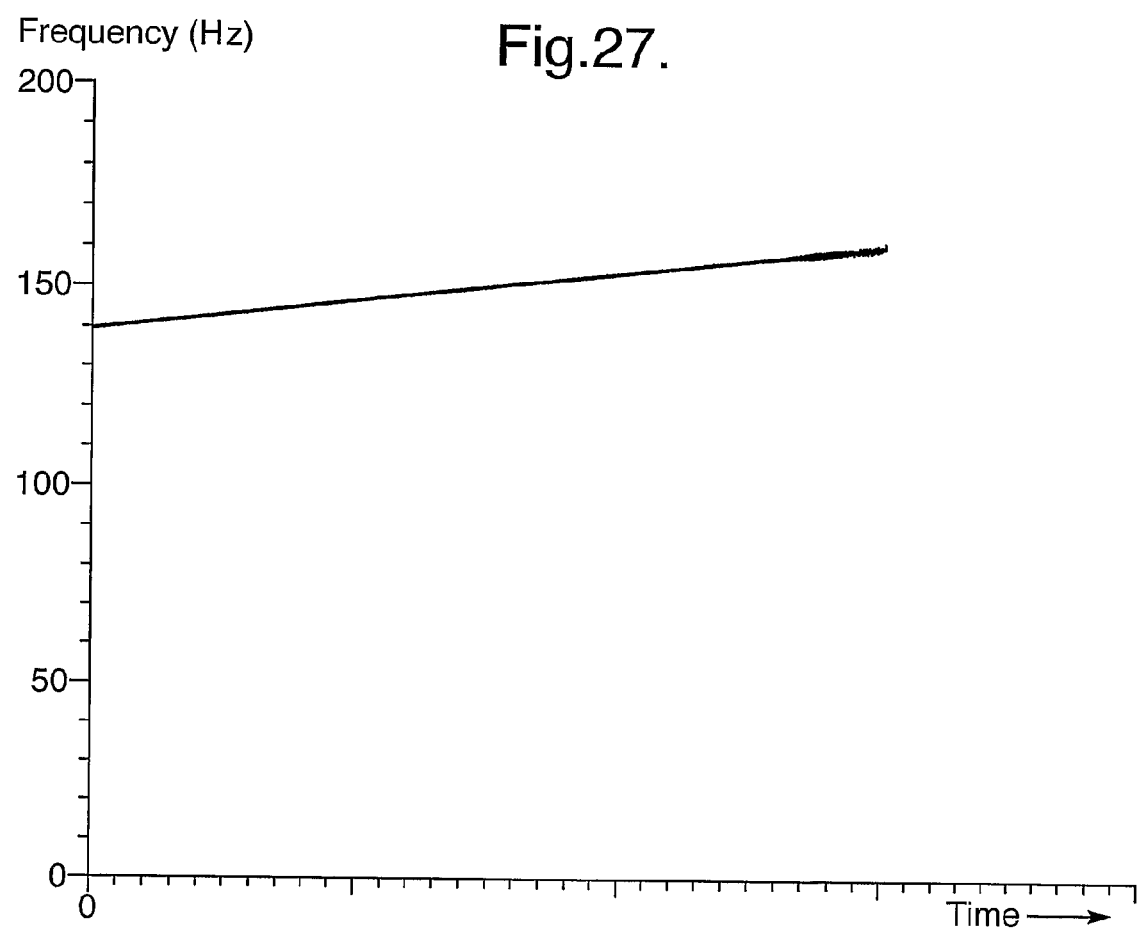
FIG. 27 shows the frequency variation of the response of the upper sideband of the response after processing according to the third embodiment.

In this embodiment, the shift frequency is chosen to be 50 Hz, with the upper sideband frequencies associated with the EO frequencies varying linearly from 140 to 160 Hz. The tracked response profile of this response is shown in FIG. 26 and may now be analysed. Analysis of this response profile gives the correct modal bandwidth of 1 Hz. The frequency of the tracked response of the upper sideband of the transformed data is shown in FIG. 27 which demonstrates the correct and continuous nature of the transformation.

Further Embodiments

Figure 30:
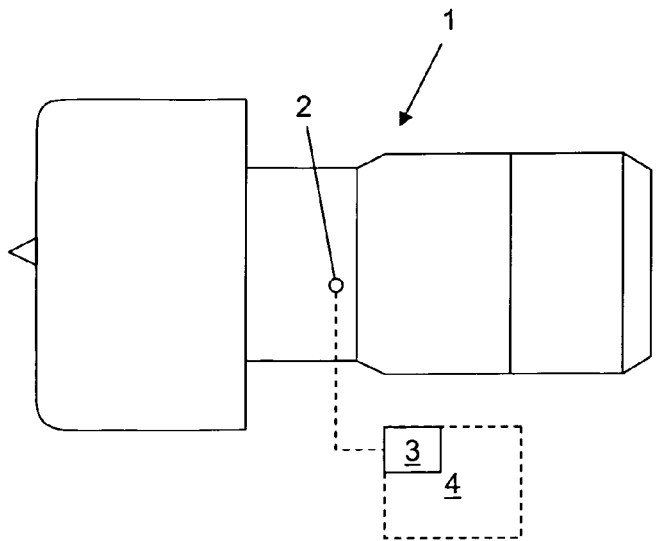
FIG. 30 shows schematically embodiments of the invention.

FIG. 30 shows schematically an embodiment of the invention, in which a gas turbine engine 1 (i.e. a resonant system) is fitted with a sensor 2 which measures oscillatory (i.e. vibration) responses of the engine. Measurement data from the sensor 2 are received by a processor 3. In another embodiment of the invention, the processor receives measurement data from a model system, in which case processor 3 is part of a computer 4.

Figure 31:
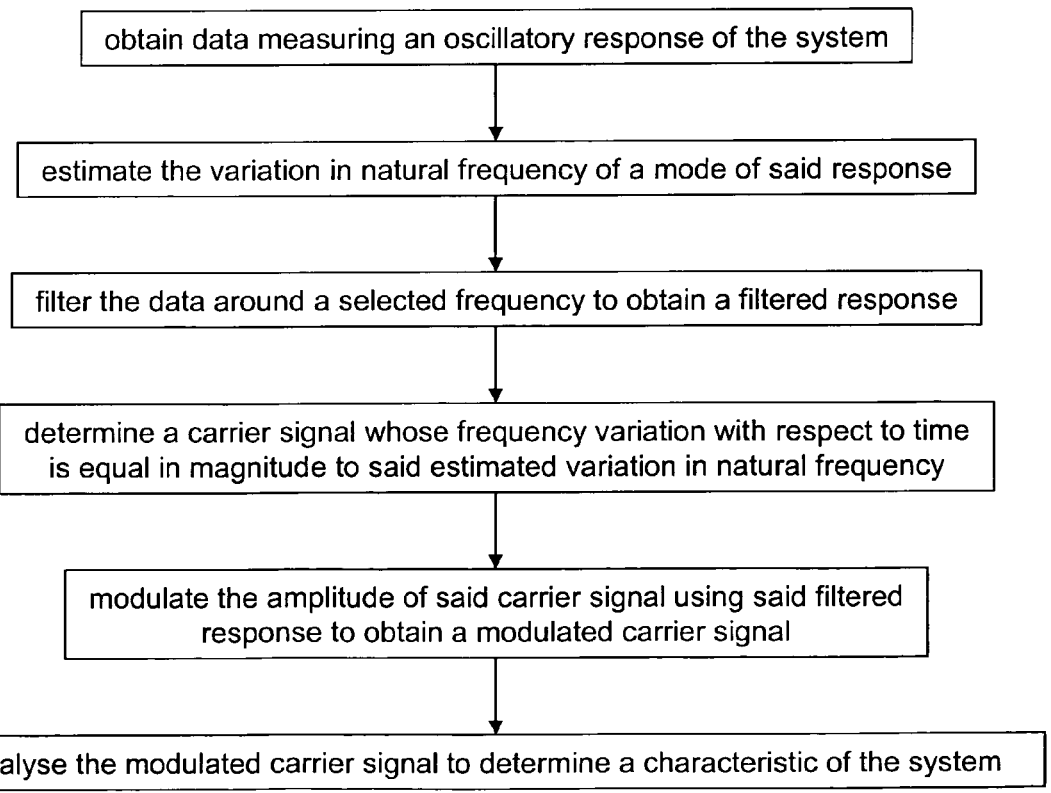
FIG. 31 is a flow chart showing steps in a method of processing oscillatory response data from a resonant system.

FIG. 31 is a flow chart showing steps in a method of processing oscillatory response data from the resonant system. The method can be performed by the processor 3.

The invention claimed is:

1. A method of processing oscillatory response data from a resonant system comprising:
    obtaining data measuring an oscillatory response of the system;
    estimating a variation in natural frequency of a mode of said response;
    filtering the data around a selected frequency to obtain a filtered response, the selected frequency being the natural frequency of said mode;
    determining a carrier signal whose frequency variation with respect to time is equal in magnitude to said estimated variation in natural frequency; and
    modulating an amplitude of said carrier signal using said filtered response to obtain a modulated carrier signal.

2. A method according to claim 1 wherein the frequency of the carrier signal is greater than a difference between the highest and lowest values of the natural frequency of said mode over a period of interest.

3. A method according to claim 1 wherein said step of estimating the variation in natural frequency includes calculating a running average of the instantaneous frequency of the response.

4. A method according to claim 1 wherein said step of estimating the variation in natural frequency includes obtaining time averaged Fourier transforms of the data measuring the oscillatory response.

5. A method according to claim 1 wherein the selected frequency is an engine order frequency.

6. A method of analysing a resonant system comprising:
    performing the method of claim 1; and
    analysing the modulated carrier signal to determine a characteristic of the system.

7. A method according to claim 6 wherein the step of analysing includes determining characteristics relating to the bandwidth of the mode.

8. A method according to claim 6 wherein the step of analysing includes determining a power spectral density function.

9. A method according to claim 1 wherein the system is a model system.

10. A method according to claim 1 wherein the system is a mechanical system.

11. A method according to claim 10 wherein the system is a gas turbine engine or a component thereof.

12. An apparatus for processing oscillatory response data from a resonant system, the apparatus including:
a processor which is configured to:
receive measurement data relating to an oscillatory response;
estimate from the data a variation in natural frequency of a mode of said response;
filter the data around a selected frequency to obtain a filtered response, the selected frequency being the natural frequency of said mode;
determine a carrier signal whose frequency variation with respect to time is equal in magnitude to said estimated change in natural frequency; and
modulate an amplitude of said carrier signal using said filtered data.

13. An apparatus according to claim 12 further including a sensor for measuring an oscillatory response of the system, wherein said processor is configured to receive said measurement data from the sensor.

14. An apparatus according to claim 13 wherein the oscillatory system is a mechanical system.

15. An apparatus according to claim 14 wherein the mechanical system is a gas turbine engine or a component thereof.

16. An apparatus according to claim 12 wherein the system is a model system, and the processor is part of a computer.

17. An apparatus according to claim 12 wherein the frequency of the carrier signal is greater than a difference between the highest and lowest values of the natural frequency of said mode over a period of interest.

18. A computer-readable recording medium encoded with a computer program for processing oscillatory response data from a resonant system, the processing including:
obtaining data measuring an oscillatory response of the system;
estimating a variation in natural frequency of a mode of said response;
filtering the data around a selected frequency to obtain a filtered response, the selected frequency being the natural frequency of said mode;
determining a carrier signal whose frequency variation with respect to time is equal in magnitude to said estimated variation in natural frequency; and
modulating an amplitude of said carrier signal using said filtered response to obtain a modulated carrier signal.

* * * * *